US005817320A

United States Patent [19]
Stone

[11] Patent Number: 5,817,320
[45] Date of Patent: *Oct. 6, 1998

[54] IN OVO IMMUNIZATION OF AVIAN EMBRYOS WITH OIL-EMULSION VACCINES

[75] Inventor: Henry D. Stone, Winterville, Ga.

[73] Assignee: The United States of America as represented by the Secretary of the Agriculture, Washington, D.C.

[*] Notice: The term of this patent shall not extend beyond the expiration date of Pat. No. 5,750,101.

[21] Appl. No.: 722,959

[22] Filed: Sep. 27, 1996

Related U.S. Application Data

[63] Continuation-in-part of Ser. No. 530,698, Sep. 15, 1995, which is a continuation-in-part of Ser. No. 269,325, Jun. 30, 1994, abandoned.

[51] Int. Cl.$^6$ .................................................. A01N 37/18
[52] U.S. Cl. .................................. 424/278.1; 424/209.1; 424/93.1; 424/93.21; 119/6.8; 119/6.9; 252/309; 252/312; 252/314
[58] Field of Search ............................. 424/278.1, 209.1, 424/93.1, 93.21; 119/6.8, 6.9; 252/309, 312, 314

[56] References Cited

U.S. PATENT DOCUMENTS

| | | | |
|---|---|---|---|
| 2,851,006 | 9/1958 | Taylor et al. | |
| 4,458,630 | 7/1984 | Sharma et al. | 119/1 |
| 5,106,617 | 4/1992 | Federicksen et al. | 424/85.2 |
| 5,176,101 | 1/1993 | Paul et al. | 119/6.8 |
| 5,206,015 | 4/1993 | Cox et al. | 424/93 |
| 5,622,649 | 4/1997 | Hunta et al. | 252/309 |

OTHER PUBLICATIONS

Avian Diseases .4:979–983, 1990. Stone et al. Efficacy of Experimental Newcastle Disease Water–in–Oil Emulsion Vaccines Formulated from Squalane and Squalene.

Avian Diseases 37:000–000, 1993. Gast et al. Evaluation of the Efficacy of Oil–Emulsion Bacterins for Reducing Fecal Shedding of *Salmonella enteritidis* by Laying Hens.

Proc. 77th Annual Meeting U.S. Animal Health Assoc. St. Louis, Missouri. 1973. pp. 596–600. Beard et al.

Nonionic Surfactants. Marcel Dekker, Inc., New York. 1966. pp. 609–611.

Avian Diseases 27:688–697, 1983. Stone et al. Influence of Formulation on the Efficacy of Experimental Oil–Emulsion Newcastle Disease Vaccines.

Avian Diseases 34:721–728, 1990. Gast et al. Serological Detection of Experimental *Salmonella enteritidis* Infections in Laying Hens.

Avian Diseases 37:1085–1091, 1993. Gast et al. Evaluation of the Efficacy of Oil–Emulsion Bacterins for Reducing Fecal Shedding of *Salmonella enteritidis* by Laying Hens.

Avian Diseases 22(4):666–674. Stone et al. Preparation of Inactivated Oil–Emulsion Vaccines with Avian Viral or Mycoplasma Antigens.

Avian Diseases 37:399–405, 1993. Stone, Henry D. Efficacy of Experimental Animal and Vegetable Oil–Emulsion Vaccines for Newcastle Disease and Avian Influenza.

Webster' II New River Side University Dictionary, 1994: 67.

*Primary Examiner*—Jasemine C. Chambers
*Assistant Examiner*—Dave Trong Nguyen
*Attorney, Agent, or Firm*—M. Howard Silverstein; John Fado; Gail E. Poulos

[57] ABSTRACT

Avian diseases, particularly those which threaten birds early in life, are controlled by embryonal vaccination using water-in-oil-in-water emulsion vaccines. The site of inoculation is the albumin end of the egg via entry through the air cell end of the egg.

7 Claims, 7 Drawing Sheets

IN OVO IMMUNIZATION OF AVIAN EMBRYOS WITH OIL-EMULSION VACCINES

This is a continuation-in-part of application Ser. No. 08/530,698, filed Sep. 15, 1995, which is a continuation-in-part of application Ser. No. 08/269,325, filed Jun. 20, 1994, abandoned, which are both herein incorporated by reference.

BACKGROUND OF THE INVENTION

1. Field of the Invention

This invention relates to in ovo treatment of avian embryos using water-in-oil-in-water (WOW) emulsion vaccines.

2. Description of the Related Art

Manual administration of emulsion vaccines to young avian flocks requires handling of individual birds and may involve corporate liability claims when self-injection occurs accidentally. Newly hatched chicks have been routinely inoculated against disease prior to being placed in brooder houses. However, vaccines do fail because the young chicks may become exposed to a virulent form of a disease before vaccination or before they have developed adequate immunity from the vaccination.

There have been a number of reports of in ovo vaccination of avian embryos. In U.S. Pat. No. 5,206,015 ('015), to Cox et al., a method is disclosed for introducing an aqueous preparation of unattenuated probiotic bacteria into the digestive tract of a bird to exclude undesirable bacteria from colonizing the digestive tract. The bacterial culture is administered by depositing it in the air cell (large end) of an egg. The digestive tract of the hatchling of the inoculated eggs is found to be colonized by the bacterial culture at the time of hatch. In this method a hole is punched into the air cell end (large end) of the egg with a first sterile needle, then the bacteria is administered using a smaller sterile needle, and finally the hole is either left unsealed or sealed with a bacteria-impermeable material.

U.S. Pat. No. 4,458,630 ('630), to Sharma et al. discloses an embryonal vaccination for Marek's disease using unattenuated turkey herpesvirus (HVT) where the injection site is within either regions defined by the amnion or yolk sac. That is, the injection is midway along, and perpendicular to, the longitudinal axis for amnion penetration through the large end of the egg with a one inch needle so that the needle passes through the outer and inner shell membranes enclosing the air cell and amnion and terminates in the fluid above the chick or in the chick itself. As in '015 patent, a hole is punched or drilled in the shell and this may be resealed with paraffin or the like.

U.S. Pat. No. 4,040,388 ('388), to Miller teaches an automated method and apparatus for injecting embryonated eggs prior to incubation with a variety of substances into the albumin end (small end) of the egg. The reference teaches coagulative cooking of the surrounding albumin to seal the hole made by the injection. The drawbacks are that the vaccine is susceptible to inactivation during the heat coagulation step. Furthermore, Sharma et al. ('630) report that albumin has an inhibitory effect on the transport of an inoculant to the embryo at the egg's opposite end.

U.S. Pat. No. 2,851,006 ('006) to Taylor et al. teaches a method for increasing the hatch rate of bacterially infected eggs by means of in ovo treatment with a suitable bacteriophage in an aqueous preparation. The phage is introduced to the interior of the egg prior to incubation by any variety of techniques including by hypodermic syringe, pressure differential in a dipping fluid and jet spray. With the hypodermic syringe, a 26 gauge short shank needle is inserted at an oblique angle into the albumin end of the egg. The patent teaches that the hole is sealed with a cellulose tape patch or a drop of melted paraffin.

In U.S. Pat. No. 3,120,834 ('834), Goldhaft et al. expands the application taught in Taylor to a variety of substances including antibiotics, sulfonamides, vitamins, enzymes, nutrients, and inorganic salts. These agents are introduced through the shell prior to incubation by means of vacuum impregnation.

U.S. Pat. No. 3,256,856 ('856) to Nicely et al. offers an improvement to the method of Goldhaft et al. in providing one or more holes in the egg shell for facilitating penetration. The hole(s) is (are) made in the air cell end (large end) of the egg, not extending beyond the inner shell membrane. The commercial practicality of the vacuum impregnation technique is limited by the unreliability of obtaining a uniform treatment and the economic unfeasibility of charging the dipping vats with expensive vaccine.

Oil-emulsion vaccines prepared with mineral oil are highly efficacious formulations used widely against poultry diseases in various monovalent and polyvalent forms. Mineral oil vaccines cause excessive tissue reactogenicity, the oil persists too long, is practically non-digestible, and is considered carcinogenic. A 42 day holding period is required before slaughter of poultry if a mineral oil vaccine is administered. Animal and vegetable oil vaccines have been developed to replace mineral oil vaccines. However, these have also resulted in tissue reactions (Stone, Avian Diseases Vol. 34:979–983. 1990; Stone, Avian Diseases Vol. 37(2) :399–405. 1993, all herein incorporated by reference).

While there are various methods for in ovo immunization using aqueous live vaccines and biologicals, there remains a need in the art for a method of in ovo immunization using oil-containing vaccines. The present invention provides a method which is different from prior art methods and overcomes problems associated with oil-containing vaccines and prior art in ovo immunization methods such as tissue reactogenicity and sealing the hole made to administer the vaccine to the embryo. Furthermore, inactivated antigens are successfully used in an in ovo oil emulsion vaccine.

SUMMARY OF THE INVENTION

It is therefore an object of the present invention to provide a method of in ovo immunization of avian embryos.

Another object of the present invention is to provide a method of in ovo immunization using oil emulsion vaccines.

A further object of the present invention is to provide a method of in ovo immunization of avian embryos with water-in-oil-in-water emulsion vaccines.

Another object of the present invention is to provide a method of in ovo immunization of avian embryos with a multivalent Water-in-oil-in-water emulsion vaccine.

A further object of the present invention is to provide a method of in ovo immunization of avian embryos with water-in-oil-in-water emulsion vaccines wherein the water-in-oil component contains a low antigen volume.

Another object of the present invention is to provide a method of in ovo immunization of avian embryos with water-in-oil-in-water emulsion vaccine where the second water components contains antisera, avian serum gamma globulin or yolk gamma globulin.

A still further object of the present invention is to provide an avian egg which includes an embryo which is immunized with a water-in-oil-in-water emulsion vaccine.

Further objects and advantages of the invention will become apparent from the following description.

BRIEF DESCRIPTION OF THE DRAWINGS

FIG. 2 shows the embryo development from 9–10 days to 18 days of age. FIGS. 2A–2C are viewed from the large end. FIGS. 2D and 2E are viewed as the egg lays on its side. The embryo at day 18 is curled around the center line which allows needle 8 to usually miss the embryo during the injection process.

DETAILED DESCRIPTION OF THE INVENTION

Figure 1:
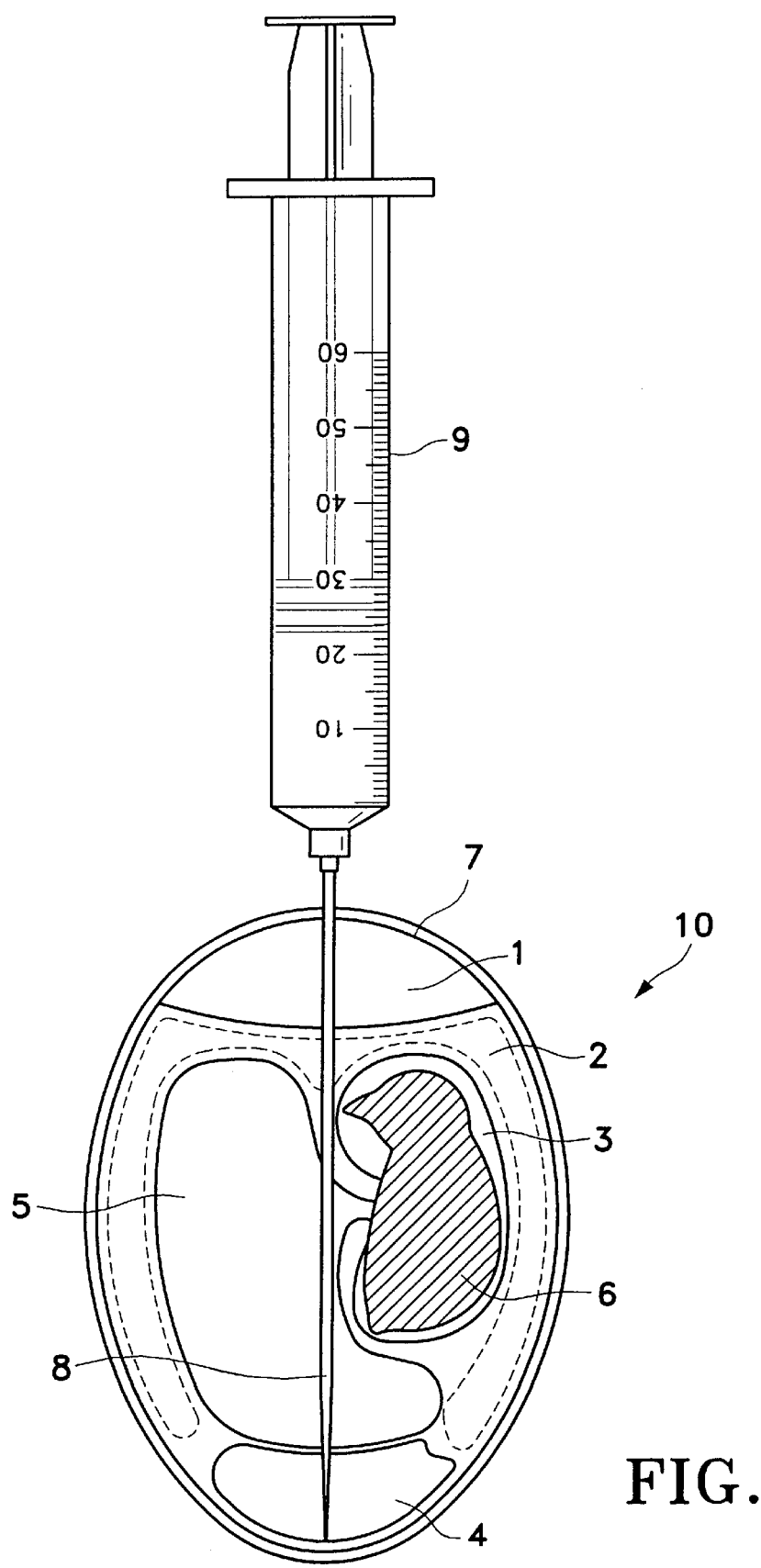
FIG. 1 shows a cross-section of chicken embryo 6 air cell end 1 up illustrating how needle 8 is placed in albumin 4 where the vaccine is deposited. The embryo 6 in the illustration is younger than when the injection actually is administered.
Figure 2C:
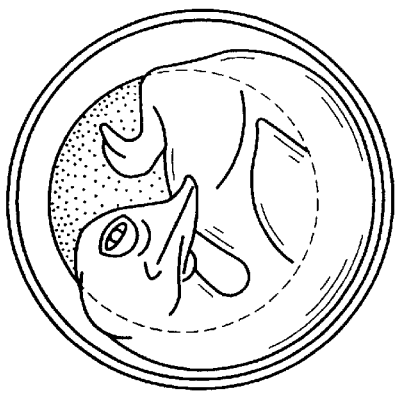
FIG. 2C shows a 15 day embryo.
Figure 2B:
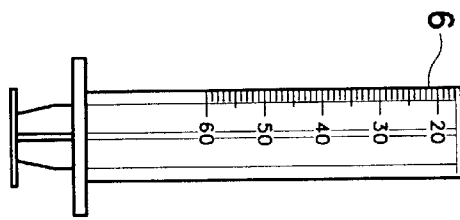
FIG. 2B shows a 13 day embryo.
Figure 2B:
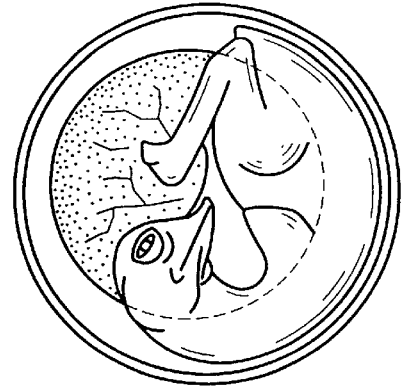
Figure 2A:
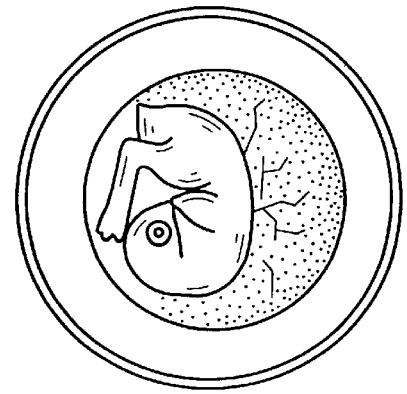
FIG. 2A shows an embryo of 9 to 10 days of age.
Figure 2E:
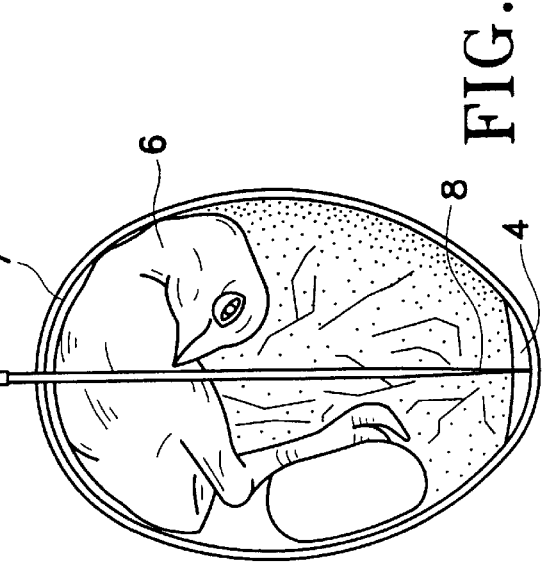
FIG. 2E shows an 18 day embryo being vaccinated.
Figure 2D:
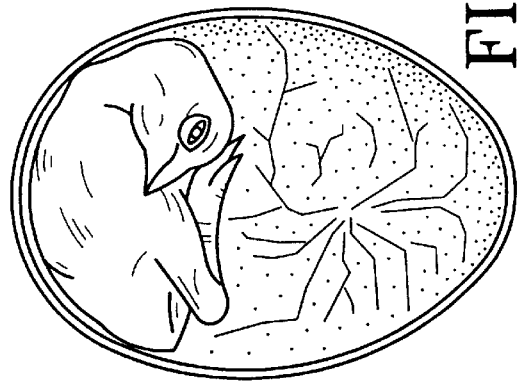
FIG. 2D shows a 17 day embryo.
Figure 3A:
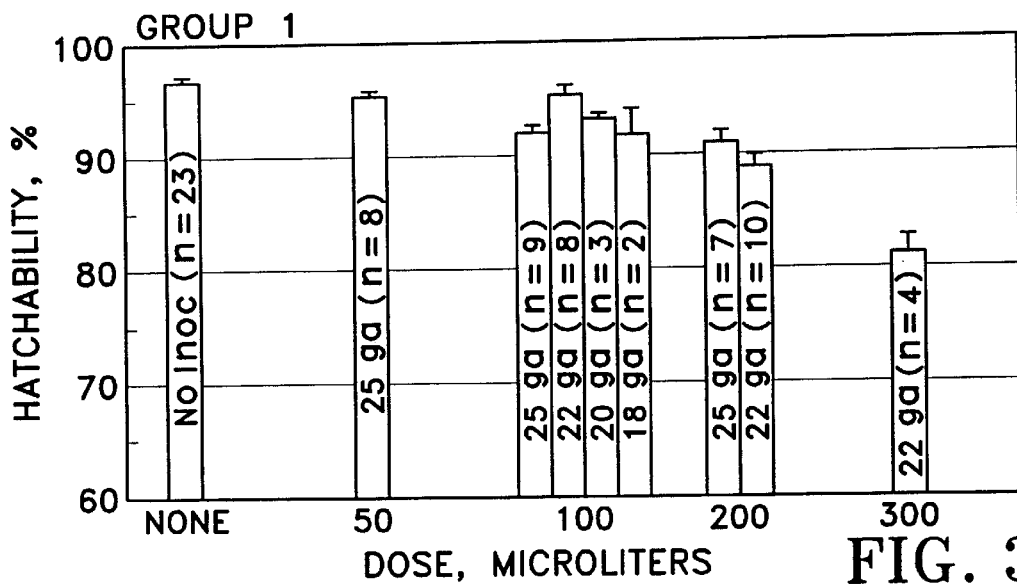
FIGS. 3a–3c are a series of graphs showing percent hatchability of white leghorn chickens vaccinated in ovo at day 18 with Newcastle Disease (ND) virus oil emulsion vaccines using different gauge needles and different doses in microliters.
Figure 3B:
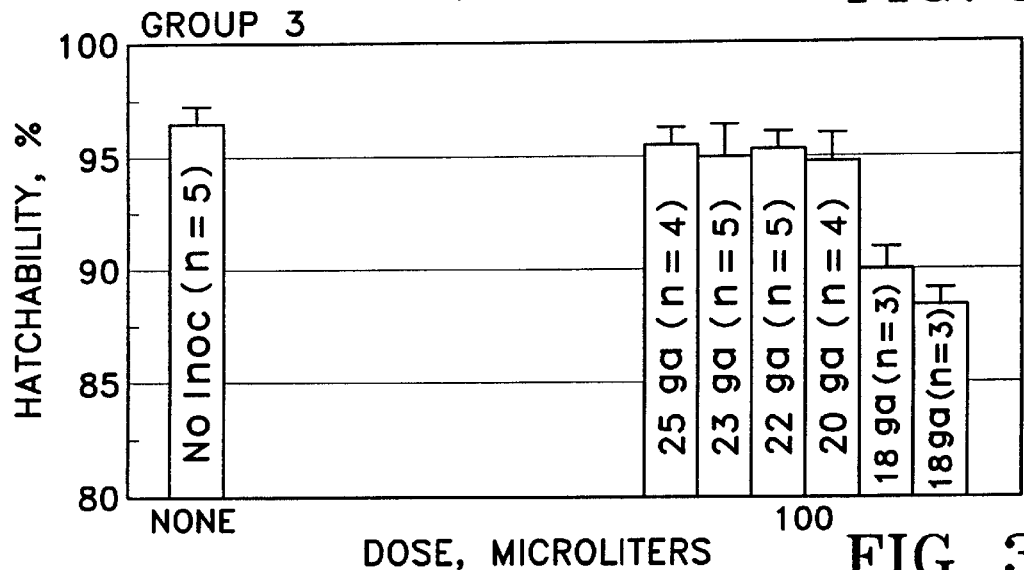
Figure 3C:
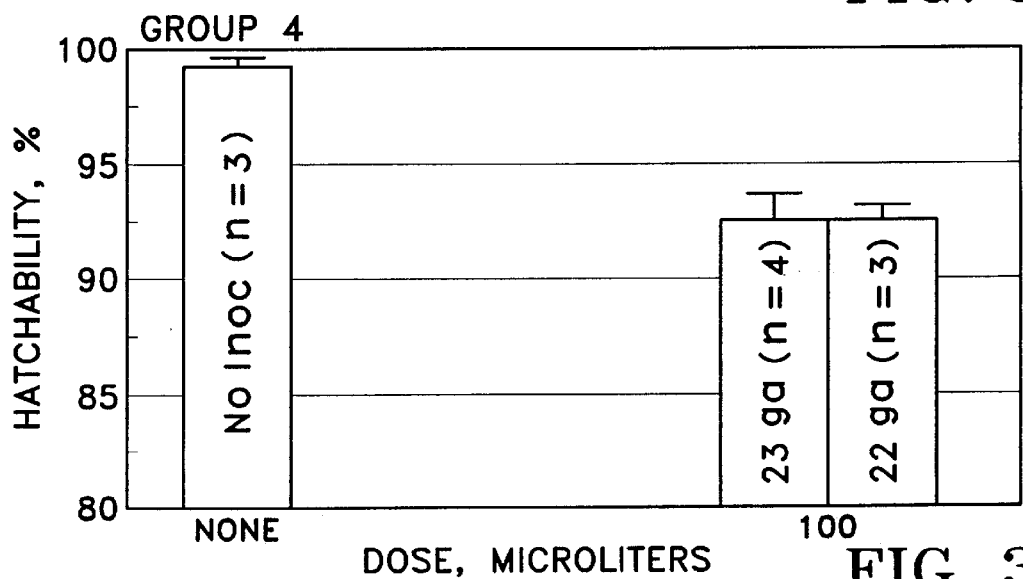
Figure 4A:
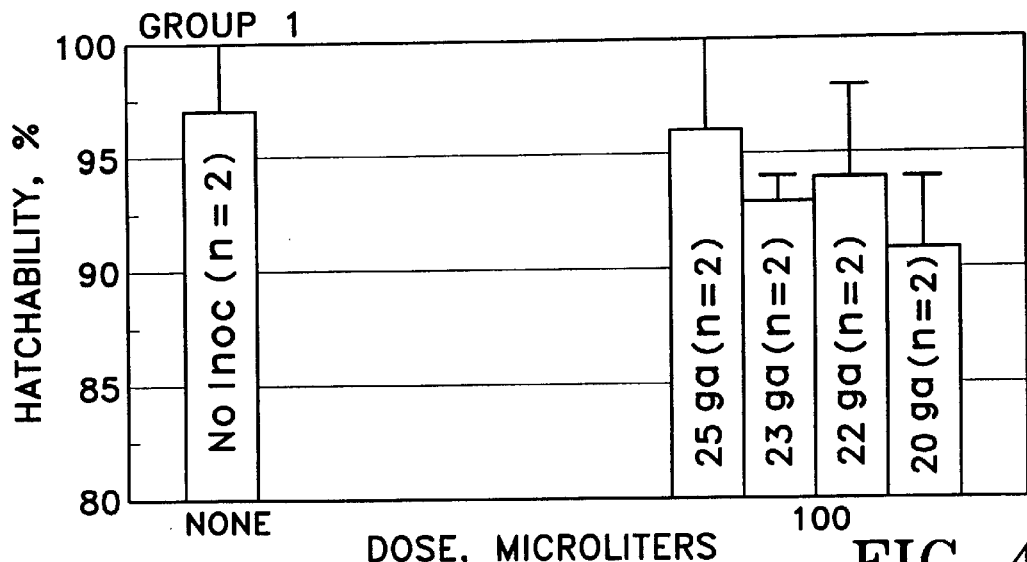
FIGS. 4a–4c are graphs showing percent hatchability of white rock chickens vaccinated in ovo at day 18 using different gauge needles at a dose of 100 microliters with a Newcastle Disease virus oil emulsion vaccine.
Figure 4B:
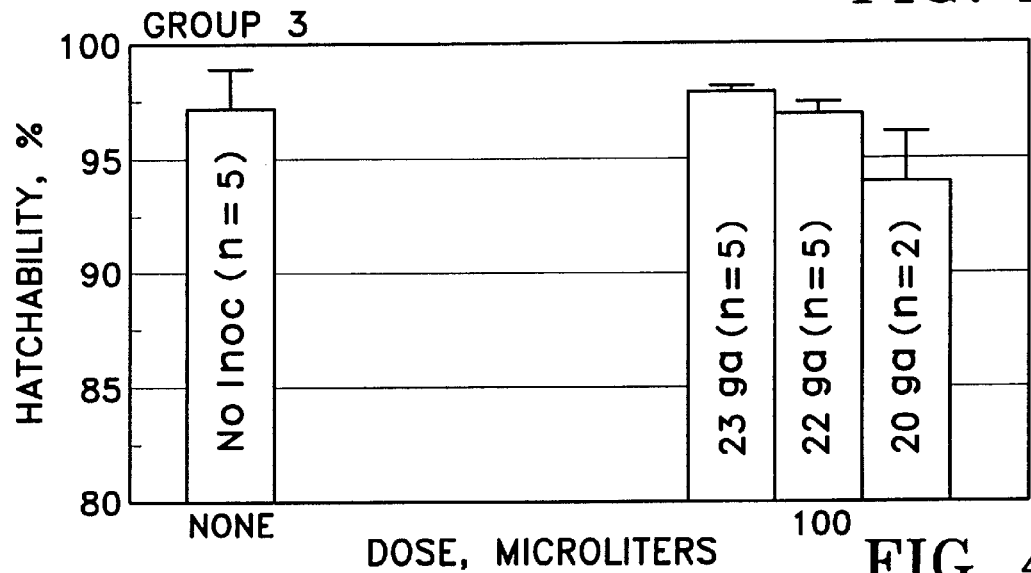
Figure 4C:
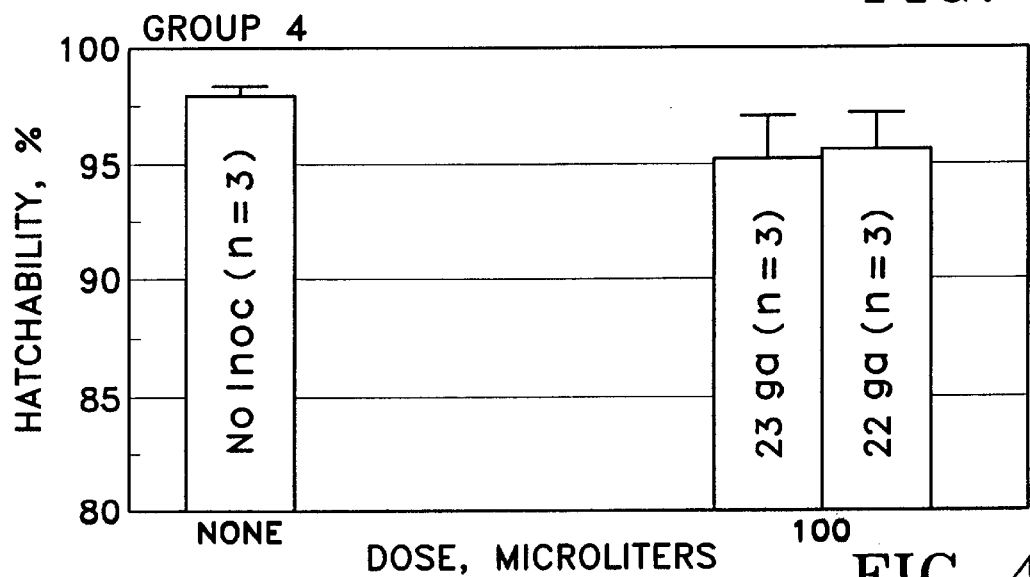

Desirable characteristics of oil emulsion (OE) vaccines are:

(a)high efficacy, (b)low viscosity, (c)long shelf life, (d)physical stability, (e)continuous monodisperse state (f)low tissue reactivity, (g)efficacy retained when different OE vaccines are mixed, (h)simple to make and upscale volume and (i)inexpensive to produce with continuous supply of components.

Antigen mass is an important factor in determining the degree of efficacy of OE vaccines. An antigen is the active ingredient of the vaccine which includes any agent which produces active immunity or competitive exclusion. When antigen mass is the only change made in a vaccine, efficacy may double when the antigen mass is doubled. However, when near maximum efficacy is reached, doubling antigen mass will only increase efficacy in slight amounts. The use of extra antigen mass also allows for deterioration over time in storage which may be 1 to 2 years or more. With the water-in-oil-in-water emulsions as herein described, there is enough volume to include a large mass of antigen in the water-in-oil component and the external aqueous phase that is either monovalent or polyvalent. The term monovalent for the purposes of this invention, means antigens from a single strain of an organism and polyvalent means antigens from more than one strain of an organism or antigens from different strains of different organisms. Live vaccine can also be included in the water phase of the WO component of the WOW emulsion vaccine. Immunostimulants can be included in the oil or water phase and made readily available to the embryo. These may extend the capability of the oil emulsion vaccine such as providing local and membrane surface immunity which is often a deficiency of emulsion vaccines with inactivated antigens. The low viscosity of the WOW emulsion vaccine is a major advantage because it allows easy injection by automated equipment and easy clean up of the injection equipment since the outer phase is aqueous.

As used herein, the terms "birds" or "avians"0 are intended to include males and females of any avian species, but is primarily intended to encompass poultry which are commercially raised for eggs or meat. Birds which are reared in high density brooder houses such as broiler and layer chickens are especially vulnerable to environmental exposure to infectious agents and would largely benefit from prehatch vaccination. Accordingly, the term "bird" or "avian" is particularly intended to encompass hens, cocks and drakes of chickens, turkeys, ducks, geese, quail, ostriches, emus and pheasants. Chicken and turkey eggs are preferred, with chicken eggs most preferred. Eggs treated by the methods of the present invention are fertile eggs which are preferably in the fourth quarter of incubation. Chicken eggs are immunized on about the fifteenth to eighteenth day of incubation (that is, the fifteenth to eighteenth day of embryonic development), and are most preferably treated on about the eighteenth day of incubation. Turkey eggs are preferably treated on about the twenty-first to twenty-sixth day of incubation, and are most preferably treated on about the twenty-fourth day of incubation. Immunocompetence in avian embryos develops in the final quarter of the incubation period.

The advantages of this invention are in the reduction and/or prevention of lethal diseases which threaten avians early in life. Avian diseases include any disease or contamination of viral, bacterial, or other microbial origin. Examples of such, without limitation thereto, include Newcastle's disease, avian leukosis, infectious bursal disease, adenovirus disease, reovirus, pox, laryngotracheitis, infectious bronchitis, reticuloendotheliosis, influenza, infectious coryza, fowl typhoid, fowl cholera, Salmonella, and Marek's disease.

The related art in ovo injection systems has shown that chickens are immune competent as late stage embryos and that the advantages of early immunization of convenience, safety, labor, and time-saving are evident. These advantages are also greatly desired for oil emulsion vaccine administration which requires even more time, labor, liability risks, and contact with chickens.

The term vaccine is defined to mean all types of biological agents used to produce active immunity or competitive exclusion.

Oil emulsion vaccines include any water-in-oil emulsion, oil-in-water emulsion, or multiple emulsion, such as water-in-oil-in-water emulsion, vaccines which are compatible with avian tissues (Gast et al., Avian Diseases Vol 37(4), 1993; Stone, Avian Diseases Vol. 37:399–405, 1993; Stone et al., Avian Diseases, Vol. 34:979–983, 1990; Stone et al., Avian Diseases, Vol. 27(3):688–697, 1983; and U.S. Pat. No. 3,919,411, Glass et al., 1975, all herein incorporated by reference).

Examples of useful oils include mineral oil, such as Drakeol 6VR; terpene oils such as squalene and squalane; vegetable oils such as soybean oil, olive oil, corn oil, jojoba oil, peanut oil, cotton-seed oil, sunflower oil, safflower oil, sesame oil, apricot oil, avocado oil, wheat germ oil, canola oil, Linseed oil, and almond oil; fish oils such as shark oil, orange roughy oil, Menhaden oil, and cod liver oil; animal oils such as mink oil, lard oil, and chicken fat oil.

Examples of surfactants used in emulsion vaccines include Arlacel 80 (sorbitan monooleate), Tween 80 (Polysorbate 80), Span 80, Arlacel 83 (sorbitan sesquioleate), Arlacel 85 (sorbitan sesquioleate), and Tween 61 (polyoxyethylene sorbitan), for example. Surfactants suitable for animal and vegetable water-in-oil vaccines include crude yellow, and purified beeswax, for example. Furthermore, surfactants suitable for vaccines containing squalene and squalane include Arlacel and Tween 80.

Metabolizable oil emulsion vaccines are also useful in the present invention and are prepared as described in U.S. patent application Ser. No. 08/384,184 which is herein incorporated by reference (Stone).

Water-in-oil-in-water (WOW) emulsion vaccines are prepared by preparing a water-in-oil (WO) emulsion first which is referred to as the primary emulsion. The primary emulsion is further emulsified in an aqueous phase that is for example, water or a buffered aqueous solution, with or without a water soluble (hydrophilic) surfactant, such as, for example, TWEEN 80, lecithin or ethoxylated castor oil. The primary emulsion is prepared in any suitable manner, such as for example, using an ultrasonicator, a laboratory mixer, etc. Comminution of the primary emulsion in the aqueous phase of the WOW emulsion is done using low-shear mixing, hand mixing or high-shear mixing.

It has been found that vaccinating and immunizing chick embryos with oil emulsion vaccines containing inactivated antigens in ovo induces protection in very young chicks through and beyond the life span of broiler chickens (>7 weeks). In methods according to the present invention, vaccines are administered into avian eggs. As used herein, "administering" includes any suitable method of in ovo delivery as is known in the art. In ovo injection to deposit a vaccine in a pre-selected location within the egg using a needle, stylus or punch inserted through the egg shell is a preferred method of administration; a pilot hole may be formed in the egg shell prior to insertion of the needle or other device which delivers the composition being administered. The vaccine is deposited on or near the inside surface of the small end 4 (albumin end) of egg 10 with needle 8 placed through the midline of the egg beginning at the large end 1 (air cell end) (see FIG. 1). Embryo 6 is curled around the center line which allows needle 8 to miss the embryo 6 proper when needle 8 follows the center line (see FIG. 2). Not all of the oil emulsion vaccine remains in the albumin 4. Since it is oil and lighter than the aqueous egg fluids, it floats upward when egg 10 is air-cell-up 1 (large end up) which is how the egg is placed for vaccination and further incubation prior to being placed on their sides in hatching trays. The vaccine becomes dispersed in the fluids of the egg by the movement of the embryo and the presence of the mixture of the surfactants which allows dispersement in aqueous medium by virtue of the surfactant hydrophilic groups. The phenomenon can be observed directly as the shell can be broken into small pieces and peeled off the chorion (the membrane next to the inner shell membrane) which encloses and keeps the entire embryo and membranes intact. The vaccine appears as milky white droplets. Furthermore, the vaccine is seen in many 1-day hatched chicks in the abdominal areas either subcutaneous (SC), intraperitoneal (IP) or in the wall of the peritoneal cavity. Before the embryo hatches, the skin completes its growth on the abdominal surface and in the process encloses the vaccine which sometimes can be seen subcutaneously in opened hatched chicks. This method simulates subcutaneous vaccination. Also as albumin 4 and yolk sac 5 enter the peritoneal cavity some of the vaccine may be enclosed intraperitoneally simulating intraperitoneal vaccination. Manual administration of emulsion vaccines to young chickens requires handling of individual chickens and may involve corporate liability when self-injection occurs accidentally.

The mechanism of injection is not particularly critical provided it does not unduly damage the tissues and organs of the embryo or the extraembryonic membranes surrounding it. A hypodermic syringe 9 fitted with a needle 8 of a gauge selected from 27, 25, 23, 22, 20, 18, and 16 gauge is suitable for the injection. A 25 gauge needle is more preferred. The length of needle 8 is dependent on the height of the egg. For example, for an average egg height of about 1 $15/16$ inches, a needle of approximately 1 ½ or 1 ¾ inches would be suitable. For an average egg height of about 2 $5/16$", a three inch needle would be suitable. Needle 8 is inserted vertically from the center of the large end 1 of a chicken egg 10 through the center line to the small end of the egg 4. For an average egg height of about 1 $15/16$ inches, a needle of about 1 ½ inches would be fully inserted. When using a needle which is longer than the egg height, needle 8 is inserted into the large end 1 of egg to the end of the small end 4 and is withdrawn from the shell a small distance in order to push the vaccine out of the needle. One of ordinary skill in the art could readily determine the needle length based on the height of the particular avian egg that will be injected.

In an automated system, it is envisioned that a penetrating device such as, for example, that taught by Miller in U.S. Pat. No. 4,040,388 or Paul et al. in U.S. Pat. No. 5,176,101 could be modified to carry out the method of the present invention. While it would not be desirable to apply heat to the needle for sterilization purposes, as suggested in the Miller patent, to the extent of inactivating the vaccine or cooking the egg's interior, sterilization between injections would be beneficial in preventing cross-contamination.

Embryonal vaccination under the aforementioned conditions is characterized by a hatch rate greater than about 80% for 18-day embryos and doses of about 300 ul or less, about 97% for groups injected with a 25 gauge needle, about 94% for groups injected with a 23 gauge needle, about 96% for groups injected with a 22 gauge needle, about 91% for groups injected with a 20 gauge needle, about 92% for groups injected with an 18 gauge needle, and about 88% for groups injected with a 16 gauge needle. Untreated eggs have a hatch rate of greater than about 95% for 18-day embryos. Furthermore, in ovo immunization with oil emulsions containing inactivated antigen confers immunity to newly hatched chicks and the vaccination persists past the hatch date.

In the present methods, an oil emulsion vaccination is administered to an egg in amounts effective to confer immunity to newly hatched and older birds in order to reduce and/or prevent lethal diseases which threaten avians early in life. Any accurate method for determining immunity in hatchling and older birds may be used as would be apparent to those skilled in the art. As used herein, "in amounts effective", "an amount effective", or an "effective amount", refer to the amount of antigen administered to confer immunity to newly hatched and/or older birds. Thus, the amount of antigen in the vaccine and/or vaccine is dependent on the disease or diseases to which the bird is being vaccinated.

The methods of the present invention also provide embryonated avian eggs which contain an oil emulsion vaccine in amounts effective to confer immunity against a desired disease.

The term "in ovo" as used herein refers to birds contained within an egg prior to hatch. Thus, the present invention may be conceived of as both a method of treating eggs as well as a method of treating a bird prior to hatch.

As used herein, incubating an avian egg to hatch refers to keeping a fertile or embryonating egg under conditions which allow the embryo to mature and hatch. As used herein, a hatchling or newly hatched bird refers to a bird that has emerged from the egg within the past seven days.

The following examples illustrate the invention and are not intended to limit the scope of the invention as defined by the claims. A Newcastle disease virus vaccine with chick embryos is used as a test model system.

EXAMPLE 1

Embryonating eggs of specific-pathogen-free (SPF) white rock and white leghorn chickens were from the USDA, Agricultural Research Services' Southeast Poultry Research Laboratory flocks which are free of Newcastle Disease, avian leukosis, infectious bursal disease, adenovirus disease, reovirus, pox, laryngotracheitis, reticuloendotheliosis, infectious coryza, fowl typhoid, fowl cholera, salmonella, avian influenza, infectious bronchitis, mycoplasma, Marek's disease, and avian encephalomyelitis antibodies. Eggs to be incubated are collected twice daily, washed and sanitized by a commercial machine at the time of collection. The eggs are held at approximately 55° F. until set (before about 10 days old), then at approximately 99.5°±5° F. and approximately 55±0.5% relative humidity. At 18 days of incubation, the embryos are candled to remove dead or unsuitable eggs. The viable eggs are randomized into groups for vaccination. Groups of vaccinated eggs were placed and hatched in separate enclosed wire hatching cages in an incubator at approximately about 99.5° F. and approximately about 55% relative humidity. Hatched chicks from each group were wing banded for identification at 1-day-old, transferred, and mixed with other hatchmate groups in a brooder battery. Chickens losing wing bands were killed and discounted from their groups. They had access to a 95°0 F. heated area with feed and water available ad libidum for two weeks and then were transferred to growing batteries. Chickens were housed in disease containment buildings with filtered air and temperature control (70° F.). Serum samples were collected at 1-week intervals from all chickens beginning 2 weeks posthatch for Hemagglutination-inhibition (HI) tests. Non-injected control eggs were used as an indication of normal hatch rates.

EXAMPLE 2

Ulster Newcastle disease virus (NDV) in allantoic fluid (hemagglutinin [HA] titer=1600, 50% embryo-lethal-dose [$ELD_{50}$]=$10^{9.1}$/0.1 ml) was propagated in 9-day-old embryos until 50% or more died, then virus containing allantoic fluid was harvested, pooled, and inactivated with 0.1% beta-propiolactone (BPL) for approximately about 2–4 hours at approximately about 24° C., and frozen (−20° C.) until used. The inactivated virus is also referred to as the antigen. Inactivation of NDV was confirmed by embryo inoculation. The antigen was also used for the hemagglutination-inhibition (HI) tests. The same antigen was used for all experiments and was undiluted.

MBL #1, an experimental Bursal Disease antigen vaccine (Maine Biological Laboratories, Inc., China Road, P.O. Box 225, Waterville, Me., 04903-0255) is prepared by growing the antigen in young chicks from which bursa, spleen, and thymus are removed after infection with infectious bursal disease, milled, inactivated, and emulsified into a mineral oil vaccine using a commercial emulsifying machine.

MBL #2 is an experimental Newcastle Disease Virus vaccine (Maine Biological Laboratories, Inc.) prepared by growing the virus in chick embryos. The embryos are finely ground and the virus inactivated. The ground tissue is then emulsified into a mineral oil vaccine using a commercial emulsifying machine. This Newcastle Disease virus is a different strain then the Ulster strain above.

Avian influenza (AI) strain A/Turkey/Wisconsin/68 (H5N9) is propagated in the allantois of 9-day-old embryonating chicken eggs by inoculation of approximately $10^3$ fifty percent egg infective doses ($EID_{50}$) of virus. The eggs are incubated for approximately about 48 hours at 37° C. and are chilled to 4° C. before allantoic fluids are harvested. The allantoic fluids contain approximately about $10^{8.9}$ embryo-lethal dose$_{50}$/0.1 ml and have a hemagglutination titer of 1:1600. Inactivation of the fluids for antigen is by treatment with 0.1% beta-propiolactone for 4 hours at approximately about 24° C. The absence of residual infectivity was confirmed by egg inoculation. The antigen is used unconcentrated and is kept at −20° C. until use. No preservatives are added to the preparation.

Avian influenza (AI) strain A/Turkey/Wisconsin/68 (H5N2) is an experimental vaccine prepared as described above for the (H5N9) Avian Influenza virus vaccine.

Salmonella enteritidis (SE) strain SE-E6 is grown up in an overnight culture of tryptic soybroth (TSB) culture. The cultures were set up as three 1.5 liter/flask cultures, each inoculated with approximately about 0.3 ml of loop picked SE from overnight nutrient agar plates. Broths are incubated at approximately about 39° C. overnight. The cultures are centrifuged to pellet the bacteria. The pellets are resuspended in 200 ml phosphate-buffered saline (PBS) and divided into 9 aliquots. Each aliquot is washed twice in PBS and the pelleted bacteria is inactivated with 10 ml of acetone for approximately about 2 hours at room temperature with occasional resuspension. Most of the acetone is removed by pipetting and the remainder is eliminated by evaporation in a desiccator under vacuum. Each tube is equivalent to 500 ml of culture. The SE antigen is kept at −20° C. until use. The antigen is diluted with PBS and the vaccine prepared as described in Example 3.

To form concentrated antigen for vaccines, the antigen preparation is concentrated by centrifugation into a button by spinning the virus down for two hours at 20,000 rpm. The button is resuspended into a smaller volume of fluid such as 1/20 to get a 20× concentration, 1/10 for 10×, etc. Chicken antisera, chicken serum gamam globulin and yolk gamma globulin, prepared from chickens immunized with New Castle disease virus, is prepared using art recognized techniques.

EXAMPLE 3

Water-in-oil (WO) emulsion vaccine was prepared with both oil-soluble surfactant, Arlacel 80 (Sorbitan monooleate) and water-soluble surfactant, Tween 80 (Polysorbate 80) added to mineral oil in a total content of about 10% and a ratio of about 3 parts Arlacel to about 1 part Tween. This ratio of surfactants provides a hydrophile-lipophile balance (HLB) of about 7.0 for best efficacy and is used for all vaccines unless otherwise indicated. See Schick, Nonionic Surfactants, Marcel Dekker, Inc., New York, N.Y., 609–611, 1966, which is herein incorporated by reference. The oil phase (oil plus surfactants) was autoclaved before vaccine emulsification. The mineral oil was Drakeol 6VR (Penreco Butler, Penn.). Oil phase to aqueous antigen (aqueous phase is allantoic fluid for NDV and AI; PBS for SE) was about 4:1 for all vaccines unless indicated otherwise.

Newcastle Disease virus metabolizable oil vaccines are prepared as described in U.S. patent application Ser. No. 08/384,184 (herein incorporated by reference).

Multivalent (polyvalent) vaccines were prepared by mixing equal parts of the monovalent vaccines together.

Water-in-oil-in-water (WOW) emulsion vaccines are prepared as follows: A water-in-oil vaccine is prepared first as described above except that the antigen phase is at least about 50% of the total volume. The oil phase contains about 20% surfactant and about 80% oil. The amount of surfactant is increased in WoW emulsion vaccines to emulsify and stabilize the large volume of antigen dispersed in droplets throughout the oil phase. The antigen mass is increased for increased efficacy and vaccine density for better dispersion in the heavier external phase which is either phosphate buffered saline (PBS) or allantoic fluid antigen harvest. The hydrophile-lipophile-balance (HBL) of the surfactants in the WO emulsion is in about a 7–10 range which greatly increases the hydrophilic affinity of the dispersed WO droplet for better dispersion in PBS or allantoic fluid and the negative charge around the WO dispersed particles which maintain separation between particles.

To form the WOW emulsion, 25 milliter quantities are prepared by mixing approximately 1 part of the WO emulsion with approximately 1 part aqueous phase manually. The aqueous phase is any water containing solution which suspends or disperses the water-in-oil component. The aqueous phase can be water, a buffered aqueous solution such as for example PBS, allantoic aqueous antigen, an aqueous vaccine with adjuvants and mixtures thereof. This mixture is then passed through various size needles or between two syringes connected by a double hub needle or canula. Larger quantities are dispersed with a blender. WO vaccines with surfactant HBLs of at least about 9 usually remain dispersed for extended periods or can be easily redispersed manually. WO vaccines of HLB less than about 9 can be dispersed easily in aqueous medium with at least about 0.5% TWEEN 80, or other water soluble surfactants such as lecithen and ethoxylated castor oil, but maintain dispersion for less time.

WO vaccines are generally made several days before use and dispersed in PBS alone or with about 0.5% to about 1% water soluble surfactant the same day or several days before use.

EXAMPLE 4

Vaccine efficacy for viral antigens is evaluated based on hemagglutination-inhibition (HI) antibody levels in serum of post-hatch chickens. HI antibody levels were determined by the microtest procedure described in Beard et al., Proceedings of the 77th Annual Meeting U.S. Animal Health Association, 596–600, 1973, which is herein incorporated by reference; using 8 HA units of NDV antigen. SE titers were determined by a SE microagglutination test described in Gast et al., Avian Diseases, vol. 34, 721–728, 1990, which is herein incorporated by reference. HI titers for ND and AI of 1:40 or above were considered indicative of protection induced by the vaccine against death. Seroconversion is also determined on the collected serum. Tests were conducted the day serum samples were taken. Chickens are also challenged from about two weeks to about 8 weeks or longer post-vaccination with a pathogen to test for early or late developing immunity HI titers, symptoms, viral isolation, and morbidity and mortality are addressed. Samples are tested the same day they were taken.

EXAMPLE 5

Groups of embryonating white leghorn and white rock chicken eggs 10 were punctured at the longitudinal midline over the air cell 7 with an egg punch and injected with mineral oil emulsion vaccine using different doses between 25 ul and 600 ul (See Tables 1, 2, 3, and 4) in the large end of the egg. The shell holes were not sealed. HI tests were conducted weekly at 2 weeks–9 weeks post hatch and at week 11.

The different variables include length of needle 8 using same average egg height (see Tables 1 and 2), in the orientation of the egg while the vaccine was being administered into the small end 4 of the egg via the large end 1, the point of entry in the egg. An HI titer of 3.0 wells or higher is considered protective. Furthermore, embryonating white leghorn chicken eggs were vaccinated as 18-day-old embryos directly through the small end 4 at different depths. The results are shown in Tables 1–5.

TABLE 1

Hemagglutination-inhibition (HI) titers post-hatch of white leghorn chickens vaccinated as 18-day-old embryos.

| Group no. | ul dose | # in group | # resp. | HI GMT weeks post-hatch of responders ||||||||| |
|---|---|---|---|---|---|---|---|---|---|---|---|---|---|
| | | | | 2 | 3 | 4 | 5 | 6 | 7 | 8 | 9 | 11 | X |
| 1 | 25 | 11 | 4 | 5.0 | 4.5 | 4.7 | 4.0 | 5.0 | — | — | — | — | 4.6 |
| 2 | 50 | 5 | 2 | 3.7 | 6.0 | 6.5 | 6.3 | 5.2 | — | — | — | — | 5.5 |
| 3 | 100 | 8 | 8 | 3.2 | 5.6 | 6.1 | 5.9 | 6.0 | 5.9 | — | — | — | 5.5 |
| 4 | 150 | 4 | 4 | 4.0 | 6.2 | 5.4 | 6.2 | 6.2 | 6.2 | — | — | — | 5.7 |
| 5 | 200 | 10 | 10 | 4.1 | 6.4 | 6.9 | 7.1 | 6.9 | 7.2 | — | — | — | 6.4 |
| 6 | 250 | 11 | 10 | 4.7 | 6.7 | 7.7 | 7.7 | 7.7 | 7.2 | 7.3 | — | — | 7.0 |
| 7 | 400 | 10 | 8 | 2.8 | 6.9 | 7.7 | 8.3 | 8.3 | 8.4 | 9.0 | 9.1 | 8.7 | 7.7 |
| 8 | 500 | 3 | 3 | 5.6 | 6.3 | 6.7 | 6.7 | 6.7 | 6.7 | — | — | — | 6.5 |
| 9 | 600 | 2 | 2 | 4.0 | 7.5 | 8.0 | 8.5 | 8.5 | 8.0 | — | — | — | 7.4 |

TABLE 1-continued

Hemagglutination-inhibition (HI) titers post-hatch of white leghorn chickens vaccinated as 18-day-old embryos.

| Group no. | ul dose | # in group | # resp. | HI GMT weeks post-hatch of responders | | | | | | | | | X |
|---|---|---|---|---|---|---|---|---|---|---|---|---|---|
| | | | | 2 | 3 | 4 | 5 | 6 | 7 | 8 | 9 | 11 | |
| 10 | none | 3 | 0 | <1 | <1 | <1 | <1 | <1 | <1 | — | — | — | <1.0 |

HItiter of 1 = 1:10, 4 = 1:80, 6 = 1:320, etc.
Notes:
1. Vaccine was Drakeol 6VR with 10% Arlacel and Tween 80 at HLB 7.0. O/A was 4:1.
2. Injection was vertical from large end through center line to small end.
3. Injection was 1-1/2 inches with 22-gauge needle.
4. Egg height was 1-15/16 inches average.
5. Hole for injection was not sealed.

TABLE 2

Hemagglutination-inhibition (HI) titers post-hatch of white leghorn chickens vaccinated as 18-day-old embryos.

| Group no. | ul dose | # in group | # resp. | HI GMT weeks post-hatch of responders | | | | X |
|---|---|---|---|---|---|---|---|---|
| | | | | 2 | 3 | 4 | 5 | |
| 1 | 100 | 10 | 8 | 3.9 | 4.3 | 6.0 | 6.3 | 5.1 |
| 2 | 200 | 9 | 6 | 4.5 | 5.7 | 6.3 | 6.5 | 5.8 |
| 3 | 300 | 8 | 7 | 3.8 | 6.9 | 7.1 | 7.1 | 6.2 |
| 4 | 400 | 3 | 3 | 4.5 | 6.5 | 6.7 | 6.0 | 5.9 |
| 5 | 500 | 9 | 9 | 4.6 | 6.6 | 8.1 | 7.4 | 6.7 |
| 6 | 200 | 11 | 8 | 4.3 | 6.1 | 7.4 | 7.3 | 6.3 |
| 7 | 300 | 7 | 6 | 3.8 | 6.6 | 6.7 | 6.5 | 5.9 |
| 8 | 400 | 7 | 6 | 4.2 | 5.2 | 7.0 | 6.7 | 5.8 |
| 9 | 500 | 2 | 2 | 4.0 | 6.5 | 7.0 | 7.0 | 6.1 |
| 10 | control | 3 | 0 | <1 | <1 | <1 | <1 | <1.0 |

HI titer of 1 = 1:10, 4 = 1:80, 6 = 1:320, etc.
Notes:
1. Vaccine was Drakeol 6VR with 10% Arlacel and Tween 80 at HLB 7.0. O/A was 4:1.
2. Group nos. 1–5 were injected with 1-1/2 inch 22-gauge needles. Group nos. 6–9 were injected with 1-3/4 inch 22-gauge needles.
3. Egg height was 1-15/16 inches average.
4. Injection was as in Table 1.
5. Hole for injection was not sealed.

TABLE 3

Hemagglutination-inhibition (HI) titers post-hatch of white rock chickens vaccinated as 18-day-old embryos.

| Group no. | ul dose | # in group | # resp. | HI GMT weeks post-hatch of responders | | | | X |
|---|---|---|---|---|---|---|---|---|
| | | | | 2 | 3 | 4 | 5 | |
| 1 | 100 | 19 | 13 | 4.4 | 4.5 | 6.0 | 5.2 | 5.0 |
| 2 | 200 | 20 | 16 | 4.2 | 5.0 | 6.3 | 6.3 | 5.5 |
| 3 | 300 | 19 | 13 | 3.8 | 4.4 | 6.0 | 6.1 | 5.1 |
| 4 | 400 | 15 | 10 | 5.1 | 6.0 | 8.4 | 6.7 | 6.6 |
| 5 | 500 | 13 | 11 | 5.0 | 6.5 | 7.6 | 8.0 | 6.8 |
| 6 | 200 | 18 | 12 | 3.0 | 5.3 | 5.9 | 5.2 | 4.9 |
| 7 | 200 | 15 | 9 | 2.9 | 5.1 | 5.8 | 5.2 | 4.8 |
| 8 | 200 | 20 | 12 | 5.2 | 5.9 | 6.3 | 6.4 | 6.0 |
| 9 | 1000 | 6 | 3 | 6.9 | 8.0 | 7.3 | 7.7 | 7.5 |
| 10 | 300 | 11 | 9 | 4.8 | 6.6 | 7.1 | 7.5 | 6.5 |
| 11 | none | 20 | 0 | <1 | <1 | <1 | <1 | <1.0 |

HI titer of 1 = 1:10, 4 = 1:80, 6 = 1:320, etc.
Notes:
1. Vaccine and injection was the same as in Table 1.
2. Egg height was 2-15/16 inches average.
3. Group no. 6 was vaccinated from top to bottom of shell with 3-inch needle.
4. Group no. 7 was vaccinated as in No. 6 with egg inverted.
5. Group no. 8 was vaccinated as in No. 2 with egg inverted.
6. Group no. 9 was vaccinated as in No. 6 with egg inverted.
7. Group no. 10 was vaccinated as in No. 3 with egg inverted.

TABLE 4

Hemagglutination-inhibition (HI) titers post-hatch of white rock chickens vaccinated as 18-day-old embryos with ND oil emulsion vaccine.

| Group no. | ul dose | # in group | # resp. | HI GMT weeks post-hatch of responders | | | X |
|---|---|---|---|---|---|---|---|
| | | | | 2 | 3 | 4 | |
| 1 | 100 | 18 | 5 | 2.0 | 4.2 | 5.4 | 3.9 |
| 2 | 200 | 15 | 6 | 3.0 | 6.3 | 6.3 | 5.2 |
| 3 | 300 | 14 | 5 | 3.5 | 5.0 | 5.8 | 4.8 |
| 4 | 400 | 12 | 9 | 3.8 | 7.0 | 7.0 | 5.9 |
| 5 | 500 | 11 | 8 | 3.4 | 4.5 | 6.3 | 4.7 |
| 6 | 1000 | 5 | 4 | 7.0 | 6.5 | 6.5 | 6.7 |
| 7 | 300 | 10 | 5 | 3.3 | 5.2 | 4.0 | 4.2. |
| 8 | 300 | 11 | 6 | 5.2 | 7.0 | 7.0 | 6.4 |
| 9 | none | 18 | 0 | 0.0 | 0.0 | 0.0 | 0.0 |

HI titer of 1 = 1:10, 2 = 1:20, 3 = 1:40, 4 = 1:80, 5 = 1:160, 6 = 1:320, 7 = 1:640
HI titers of 1:40 or above are considered protective
Notes:
1. Injection was perpendicular from the large end of egg through the mid-line to the bottom inside surface of the small end.
2. Needles were 22-gauge, 3-inches long.
3. In group No. 7 the eggs were inverted then injected as described in Example 5.
4. In group No. 8 the eggs were injected horizontally from large end to small end.
5. Flock was at end of lay:
6. Egg height 2-5/32'.

TABLE 5

Hemagglutination-inhibition (HI) titers post-hatch of white leghorn chickens vaccinated as 18-day-old embryos with Newca Disease (N.D) oil-emulsion (OE) vaccine given at different depths through the small end.

| Group | Depth of | Total CE | No. | % | # per | No. | % | Geometric Mean HI Titers Weeks (posthatch) | | | Mean |
|---|---|---|---|---|---|---|---|---|---|---|---|
| Number | Inj. | Inj. | Hatch | Hatch | Group | Reponse | Response | 2 | 3 | 4 | Titer |
| 1 | 1/4" | 20 | 19 | 95 | 15 | 0 | 0 | 0.0 | 0.0 | 0.0 | 0.0 |
| 2 | 1/2" | 20 | 18 | 90 | 15 | 5 | 33 | 4.0 | 4.8 | 4.8 | 4.5 |
| 3 | 1" | 20 | 16 | 80 | 15 | 10 | 67 | 4.4 | 5.6 | 5.6 | 5.2 |
| 4 | 1-1/2" | 20 | 18 | 90 | 15 | 8 | 53 | 3.9 | 4.9 | 5.4 | 4.7 |
| 5 | None-Ctrl | 25 | 24 | 96 | 24 | 0 | 0 | 0.0 | 0.0 | 0.0 | 0.0 |

Notes:
1. Needles were 20 gauge 1/4", 1/2", 1", and 1-1/2" respectively for groups 1, 2, 3, and 4.
2. Egg fluid was expelled when vaccine was administered at 1/4", 1/2" and 1" depths.
3. Eggs were vertical with small end up.
4. Holes were not sealed.
5. Vaccine dose was 100 ul.

EXAMPLE 6

52-day-old white leghorn chickens were challenged with the lethal Fontana strain of velogenic viscerotropic Newcastle disease virus (VVNDV) at 8 weeks post-vaccination as 18-day-old embryos. The embryos received a 200 ul dose of the mineral oil emulsion with Ulster NDV antigen prepared as described in Examples 2 and 3 above. The mean HI titer at the time of challenge was 7.2. Individual post-hatch titers of each of the ten chickens is reported in Table 5 below. VVNDV was given intraocularly in a 0.1 ml volume containing $10_{7.3}ELD_{50}$. Chickens were observed over a two week period for morbidity and mortality. Vent and tracheal swabs were taken 5 and 14 days postchallenge for virus isolation and HI titers were determined as described above. The results are reported in Table 6 below.

EXAMPLE 7

At the end of the experiments, all in ovo vaccinated chickens were sacrificed and examined in the abdominal cavity or the breast muscle for the formation of lesions which were induced by the immunization. A lesion is defined as discolored, demarcated, inflamed, edematous, granulomatous, indurated, or necrotic tissue; or if tissue contained either encapsulated or diffuse vaccine. Usually, when a newly hatched chicken is vaccinated using a mineral oil emulsion vaccine, lesions appear as early as one week. In the in ovo immunized chickens, there was no evidence of gross lesions in any of the meat even after 11 weeks post-hatch. None of the meat would have been condemned for meat consumption.

TABLE 6

Challenge response of 52-day-old white leghorn chickens to velogenic viscerotropic Newcastle disease (VVNDV) at 8-weeks postvaccination as 18-day-old embryos.

| Chicken | HI titer at weeks post-hatch | | | | | | Mean | Virus isolation | | No. alive/Total no. | |
|---|---|---|---|---|---|---|---|---|---|---|---|
| Number | 2 | 3 | 4 | 5 | 6 | 7 | titer | oral | cloaca | controls | vaccination |
| 1 | 3 | 8 | 8 | 8 | 8 | 8 | 7.2 | – | – | 0/55 | 10/10 |
| 2 | 4 | 4 | 5 5 | 5 | 6 | 4.8 | + | – | | | |
| 3 | 4 | 7 | 6 5 | 6 | 6 | 5.7 | + | – | | | |
| 4 | 4 | 8 | 8 9 | 8 | 8 | 7.5 | + | – | | | |
| 5 | 4 | 8 | 8 8 | 8 | 8 | 7.3 | + | – | | | |
| 6 | 6 | 7 | 6 6 | 6 | 6 | 6.2 | – | – | | | |
| 7 | 4 | — | 7 7 | 6 | 6 | 6.0 | + | – | | | |
| 8 | 6 | 8 | 8 9 | 8 | 9 | 8.0 | + | – | | | |
| 9 | 6 | 8 | 8 9 | 8 | 9 | 8.0 | – | – | | | |
| 10 | <1 | <1 | 5 | 5 | 5 | 6 | 3.5 | + | – | | |
| | | | | | | | | 7/10 | 0/10 | | |
| controls | | | | | | | | | | | |
| 11 | <1 | <1 | <1 | <1 | <1 | <1 | <4.0 | ND | ND | | |

Notes:
1. Challenge was $10^{7.3}$ VVNDV in 0.1 ml given intraocularly.
2. Observation period was 2 weeks.
3. Virus isolation attempts were made at 5 days postchallenge.
4. There was no morbidity in the vaccinates.
5. Vaccine dose was 0.2 ml of mineral oil emulsion with Ulster NDV (0.1% BPL).
6. All unvaccinated controls died.

EXAMPLE 8

The HI titers of post-hatch white leghorn chickens vaccinated in ovo were compared to that of chicks vaccinated at 1-day-old. 18-day and 19-day embryos as well as 1-day-old chicks were vaccinated with 200 ul of the Newcastle disease oil-emulsion vaccine prepared as described in Examples 2 and 3 above. 1-day old chicks received 200 ul of the vaccine subcutaneously in the nape of the neck region. 18-day and 19-day embryos were vaccinated as described in Example 5. The results are reported in Table 7 below.

described in Examples 2 and 3 above and in different oil phase/aqueous antigen (0/A) ratios (see Tables 8 and 9 below). The vaccine was also placed at different depths in the egg. The results are shown in Tables 8 and 9 below.

TABLE 7

Hemagglutination-inhibition (HI) titers post-hatch of white leghorn chickens vaccinated as 18- or 19-day-old chick embryos (CE) or 1-day-old chicks with Newcastle Disease (ND) oil-emulsion vaccine.[A]

| Group Number | No. CE | No. Hatch | % Hatch | No. Response/ Total | Percent Response | 2 | 3 | 4 | 5 | 6 | Mean Titer |
|---|---|---|---|---|---|---|---|---|---|---|---|
| TRIAL 1 | | | | | | | | | | | |
| 1 Antigen only | 20 | 19 | 95 | 0/19 | 0 | 0.0 | 0.0 | 0.0 | 0.0 | — | 0.0 |
| 2 18-day-CE | 20 | 17 | 85 | 10/17 | 59 | 4.6 | 4.9 | 7.0 | 6.8 | — | 5.8 |
| 3 19-day-CE | 20 | 16 | 80 | 9/16 | 56 | 3.9 | 6.5 | 5.6 | 5.6 | — | 5.4 |
| 4 1-day-chick | 20 | 20 | 100 | 18/20 | 90 | 4.2 | 7.8 | 7.5 | 7.6 | — | 6.8 |
| 5 No vacc. Ctrl. | 20 | 18 | 90 | 0/18 | 0 | 0.0 | 0.0 | 0.0 | 0.0 | — | 0.0 |
| 6 Needle only injection | 20 | 17 | 85 | ND | — | — | — | — | — | — | — |
| TRIAL 2 | | | | | | | | | | | |
| 7 18-day-CE | 20 | 17 | 85 | 10/15 | 67 | 5.0 | 5.6 | 6.2 | 6.4 | 6.2 | 5.9 |
| B 19-day-chick | 20 | 10 | 100 | 10/10 | 100 | 5.2 | 6.8 | 7.8 | 7.9 | 7.6 | 7.1 |
| 9 No vacc. Ctrl. | 20 | 20 | 100 | 0/20 | 0 | 0.0 | 0.0 | 0.0 | 0.0 | 0.0 | 0.0 |

[A]Embryos received 200 ul of vaccine full depth on center line from large end to small end of egg. One-day-old chicks received 200 ul of vaccine subcuteneously in nape of neck region.

EXAMPLE 9

White rock chicken embryos from flocks at the beginning of lay and flocks at the end of lay were vaccinated at 14 to 18 days using different amounts of the vaccine preparation

TABLE 8

Hemagglutination-inhibition (HI) titers post-hatch of white rock chickens vaccinated as embryos at 18 days at different depths with Newcastle disease (ND) oil-emulsion vaccine.

| Group Number | Percent Hatch | No. Tested | % Resp. | Depth of Injection | Percent Avg. Depth in Egg | ul Dose | Vaccine O/A Ratio | 3 | 4 | 5 | X |
|---|---|---|---|---|---|---|---|---|---|---|---|
| 1 | 79 | 13 | 92 | 1-1/2 | 76 | 200 | 4:1 | 6.4 | 6.9 | 6.2 | 6.5 |
| 2 | 85 | 18 | 89 | 1-3/4 | 89 | 200 | 4:1 | 6.8 | 7.5 | 7.1 | 7.1 |
| 3 | 85 | 18 | 89 | 2 | 100 | 200 | 4:1 | 6.7 | 7.0 | 7.0 | 6.9 |
| 4 | 85 | 16 | 69 | full | 100 | 200 | 4:1 | 5.2 | 5.6 | 6.6 | 5.8 |
| 5 | 100 | 20 | 94 | 1-1/2 | 76 | 200 | 60:40 | 7.4 | 8.1 | 7.6 | 7.7 |
| 6 | 90 | 17 | 100 | 1-3/4 | 89 | 200 | 60:40 | 8.2 | 7.5 | 6.9 | 7.5 |
| 7 | 70 | 17 | 65 | 2 | 100 | 200 | 60:40 | 5.2 | 6.7 | 7.2 | 6.4 |
| 8 | 100 | 19 | 80 | full | 100 | 200 | 60:40 | 6.1 | 6.8 | 5.5 | 6.1 |
| 9 | 80 | 6 | 67 | 1-3/4 | 89 | 300 | 4:1 | 7.0 | 8.0 | 7.0 | 7.3 |
| 10 | 90 | 15 | 71 | 2 | 100 | 200 | 4:1 | 7.1 | 7.5 | 7.2 | 7.3 |
| 11 | 95 | 17 | 88 | 1-3/4 | 89 | 300 | 60:40 | 6.9 | 7.5 | 7.3 | 7.2 |
| 12 | 70 | 10 | 82 | 2 | 100 | 300 | 60:40 | 5.6 | 7.4 | 5.6 | 6.2 |
| 13-Ctrl | 100 | — | — | — | — | — | — | — | — | — | — |

HI titer of 1 = 1:10, 2 = 1:20, 2 = 1:40, etc.
Notes:
1. Flock was at beginning of lay.
2. Injection was from large end in center line to small end of egg.
3. 22-gauge, 2-inch needlee.
4. Egg height was 1-31/32" average.
5. Vaccine was Drakeol 6VR HLB 7, 10% (Arl 80 and Tween 80) in oil phase, O:A = 4:1, Ulster NDV.

TABLE 9

Hemagglutination-inhibition (HI) titers post-hatch of white rock chickens
vaccinated as embryos at 14 to 18 days and at
different depths with Newcastle disease (ND) oil-emulsion vaccine.

| No. & age of group | No. Eggs Per Group | % Hatch | No. Hatched | No. Tested | Percent Responders | Depth of Injection | Percent Average Depth of Egg | HI GMT weeks posthatch of responders | | | |
|---|---|---|---|---|---|---|---|---|---|---|---|
| | | | | | | | | 2 | 3 | 4 | X |
| 1. 14-day | 16 | 44% | 7 | 6 | 0.0 | Full | 100 | 0.0 | 0.0 | 0.0 | 0.0 |
| 2. 15-day | 20 | 70% | 14 | 10 | 20.0 | Full | 100 | 4.5 | 5.0 | 6.0 | 5.2 |
| 3. 16-day | 19 | 74% | 14 | 10 | 0.0 | Full | 100 | 0.0 | 0.0 | 0.0 | 0.0 |
| 4. 17-day | 18 | 72% | 13 | 11 | 36.0 | Full | 100 | 6.3 | 6.3 | 6.3 | 6.3 |
| 5. 18-day | 20 | 75% | 15 | 13 | 62.0 | Full | 100 | 4.4 | 5.5 | 5.6 | 5.2 |
| 6. 18-day | 25 | 84% | 21 | 14 | 14.0 | 1" | 46 | 2.7 | 5.6 | 5.5 | 4.6 |
| 7. 18-day | 25 | 76% | 19 | 15 | 75.0 | 1-1/4" | 58 | 3.7 | 5.3 | 5.1 | 4.7 |
| 8. 18-day | 25 | 80% | 20 | 17 | 71.0 | 1-1/2" | 70 | 5.8 | 6.5 | 6.5 | 6.3 |
| 9. 18-day | 24 | 71% | 17 | 12 | 75.0 | 1-3/4" | 81 | 6.2 | 7.0 | 6.9 | 6.7 |
| 10. 18-day | 25 | 60% | 15 | 12 | 92.0 | 2" | 93 | 5.6 | 6.3 | 6.1 | 6.0 |
| 11. 18-day | 20 | 100% | 20 | 11 | 62.0 | 1/8" off full | | 94 | 4.7 | 6.0 | 6.3 | 5.7 |
| 12. 18-day | 19 | 95% | 18 | 15 | 75.0 | 1/8" off full | | 94 | 6.5 | 5.9 | 5.8 | 6.1 |
| 13. Uninoculated | 23 | 83% | 19 | — | — | — | — | — | — | — | — |

HI titer of 1 =1:10, 2= 1:20, 3 = 1:40, 4 = 1:80, 5 = 1:160, 6 = 1:320, 7 = 1:640
HI titers of 1:40 or above are considered protective.
Notes:
1. Vaccine dose was 0.2 ml per each egg given perpendicularly through mid-line, large end toward small end.
2. Needles were 22-gauge, 3 inches long.
3. Egg height was 2-5/32 inches average.
4. Flock was at end of lay.
5. Vaccine was mineral oil with 10% surfactant (4 parts) and 1 part NDV Ulster inactivated (0.1% BPL) antigen emulsified in a Waring blender. HLB of 7.

EXAMPLE 10

18-day-old white leghorn chick embryos (CE) were injected as described in Example 5 with varying amounts of oil emulsion vaccines containing inactivated avian influenza (AI) virus, Newcastle disease (ND) virus, and Salmonella enteritidis (SE). Furthermore, a polyvalent vaccine was prepared by mixing equal parts of the three monovalent vaccines together. The O/A ratio for all the vaccines was 4:1 and the HLB=7. The inactivated antigens were prepared as described in Example 2 above and the oil emulsion prepared as described in Example 3. Titers for AI and ND are hemagglutination-inhibition titers and SE titers are microagglutination titers as described in Example 4 above. The results are reported in Table 10 below. NDV and AI titers of 1:40 or above are considered indicative of protection against death. The SE titers show sensitization has occurred and hatched chickens can be revaccinated with SE for high sustained titers.

TABLE 10

Vaccination of 18-day-old white leghorn chick embryos (CE) with monovalent
and polyvalent oil emulsion (OE) of avian influenza
(AI) Newcastle Disease (ND) and *Salmonella enteritidis* (SE)

| Group Number | OI Vaccine | ul Dose | No. CE Inj. | No. CE Hatch | No. Total Response | Percent Responders | GM Titers of Responders Weeks - Postvaccination | | | | Mean Titer |
|---|---|---|---|---|---|---|---|---|---|---|---|
| | | | | | | | 2 | 3 | 4 | 5 | |
| 1 | AI | 100 | 20 | 16 | 10/15 | 67 | 2.2 | 3.2 | 5.5 | 5.5 | 4.4 |
| 2 | AI | 200 | 20 | 17 | 08/15 | 53 | 5.4 | 5.7 | 6.3 | 7.7 | 6.3 |
| 3 | AI | 300 | 20 | 17 | 09/17 | 53 | 3.0 | 4.0 | 5.9 | 6.9 | 5.0 |
| 4 | ND | 200 | 20 | 17 | 11/15 | 73 | 4.6 | 4.9 | 7.0 | 6.8 | 5.8 |
| 5 | SE | 100 | 20 | 14 | 12/13 | 92 | 4.1 | 4.5 | 3.4 | 3.5 | 3.9 |
| 6 | SE | 200 | 20 | 18 | 14/18 | 78 | 5.0 | 5.1 | 5.0 | 4.7 | 5.0 |
| 7 | Poly (AI,ND,SE) 1:1:1v:v:v: | 300 | 20 | 17 | | | | | | | |
| | AI | 100 | | | 14/17 | 82 | 2.0 | 4.3 | 6.1 | 6.8 | 4.8 |
| | ND | 100 | | | 13/17 | 76 | 4.1 | 7.1 | 6.1 | 6.1 | 5.9 |
| | SE | 100 | 15/17 | 88 | 3.5 | 5.9 | 3.6 | 3.6 | 4.2 | | |

[A]Polyvalent vaccine was formed by adding equal parts of preformed HI, ND, and SE oil emulsion vaccines together
[B]No. of responders is the greatest no. to respond during any bleeding weeks posthatch.
[C]Titers for AI and ND are hemagglutination-inhibition titers.
Titers for SE are microagglutination titers.

EXAMPLE 11

Groups of embryonating white leghorn and white rock chicken eggs 10 were injected as described in Example 5 above with Ulster ND virus mineral oil or metabolizable oil emulsion vaccines using different doses between 50 microliters and 300 microliters and different gauge needles between 27 gauge and 16 gauge. Injection depth was 1.5 inches. Group 1 and 3 chicken embryos received a vaccine preparation as described in Example 3 to determine hatchability rates. Group 3 vaccine differs in the lot number of Arlacel 80 being a more pure preparation than the one used in group 1. Group 2 chicken embryos received a metabolizable oil emulsion vaccine as described above in Example 4. Results are shown in FIGS. 3a–3c and 4a–4c.

In pooled groups, hatchability was 97% for unvaccinated controls, 97% for groups injected with a 25 gauge needle, 94.5% for groups injected with a 23 gauge needle, 96.5% for groups injected with a 22 gauge needle, 91% for groups injected with a 20 gauge needle, 92.5% for groups injected with an 18 gauge needle, and 88% for groups injected with a 16 gauge needle.

EXAMPLE 12

Groups of embryonating white leghorn (WL) chickens were injected as described above in example 5 using a 22 gauge needle. The vaccines used were the A/turkey/Wisconsin/68 (H5N2) influenza monovalent oil emulsion vaccine, TW68, an experimental vaccine obtained from Maine Biological Laboratories, a monovalent ND oil emulsion vaccine using the ulster Newcastle Disease mineral oil emulsion vaccine described above, and 2 multivalent vaccines using experimental oil emulsion vaccine preparations, MBL #1 (Bursal Disease vaccine) and MBL #2 (Newcastle Disease vaccine) (Both from Maine Biological Laboratories, Inc.) along with the Ulster Newcastle disease antigen, prepared as described above in Example 2. Addition of Ulster Newcastle Disease vaccine to the MBL #1 and #2 demonstrates the capability to form combined vaccines of different antigens or boost the efficacy of vaccines of "like" antigens.

Figure 5:
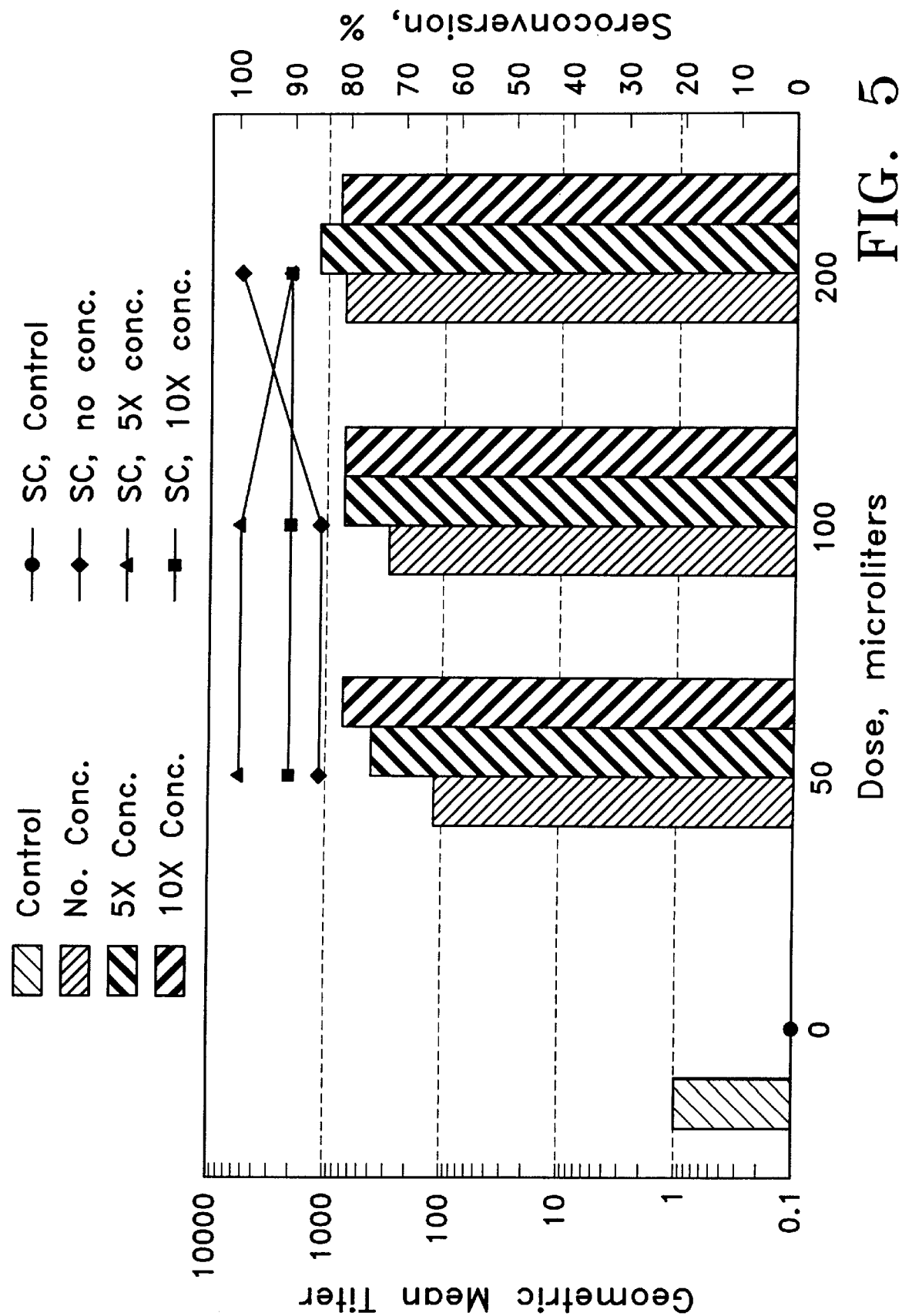
FIG. 5 is a graph showing geometric mean titers and seroconversion of white leghorn (WL) chickens vaccinated in ovo at day 18 with an experimental A/turkey/Wisconsin/68 influenza monovalent oil emulsion vaccine, TW68, using different concentrations of antigen and different doses in microliters using a 22 gauge needle.
Figure 6:
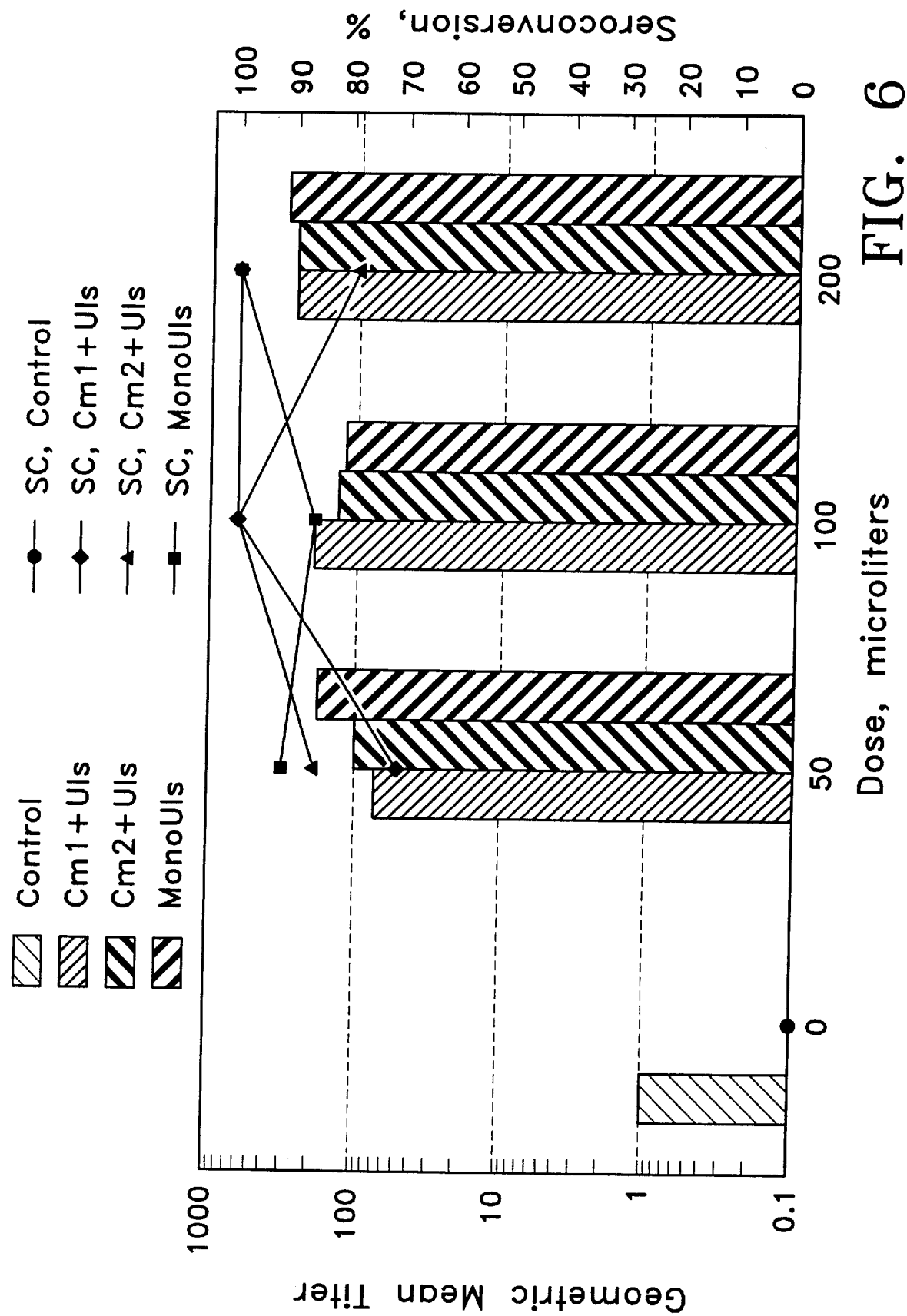
FIG. 6 is a graph showing geometric mean titers and seroconversion white leghorn (WL) chickens vaccinated in ovo at day 18 using an Ulster ND monovalent oil emulsion vaccine and the Ulster vaccine together with one of two experimental inactivated vaccines from a commercial company (Maine Biologics Laboratory) to form two multivalent vaccines.
Figure 7:
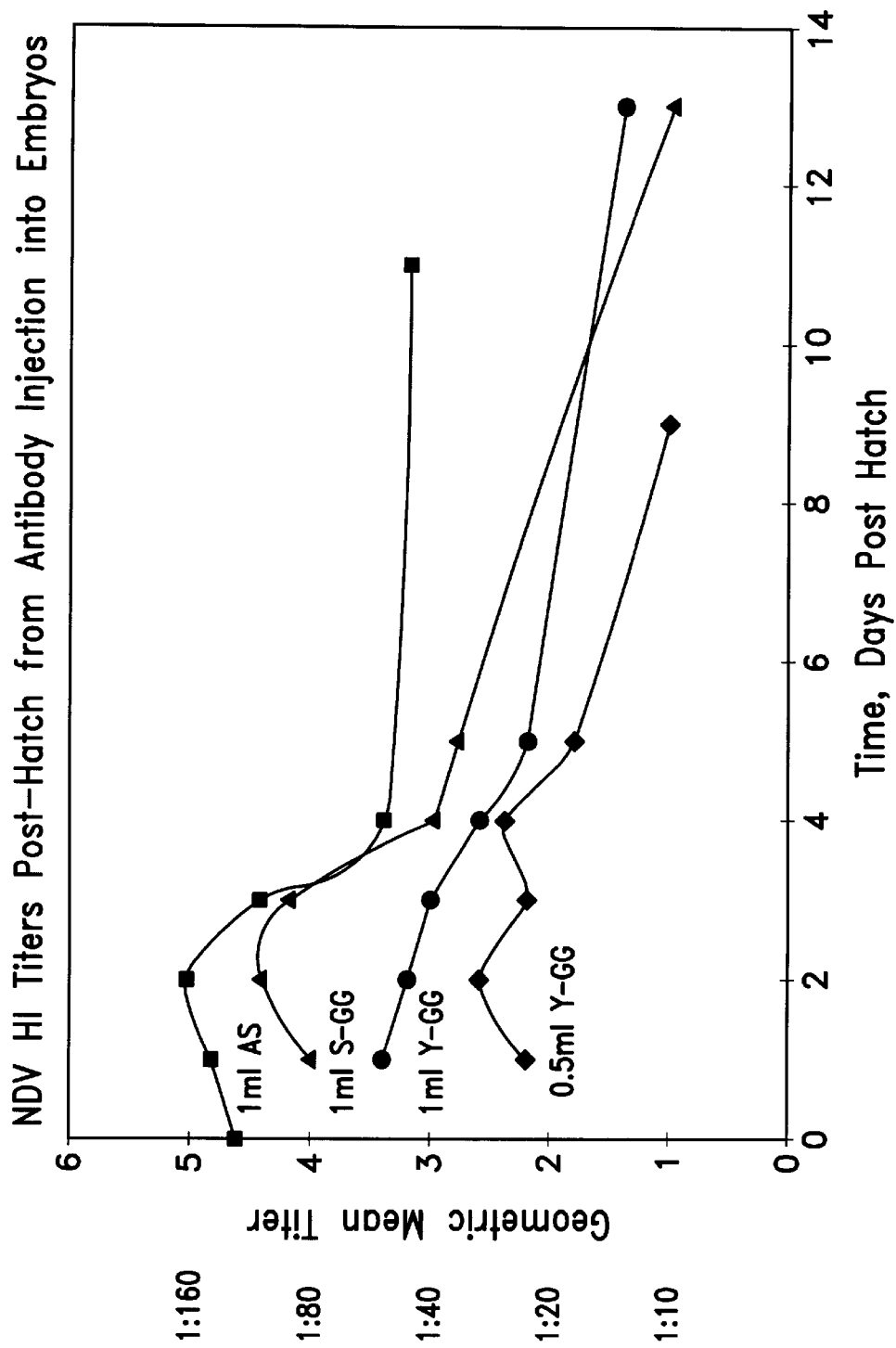
FIG. 7 is a graph showing Newcastle Disease Virus (NDV) HI-titers post-hatch from embryos injected with chicken antiserum, chicken serum gamma globulin and yolk gamma globulin.

Vaccine efficacy at different doses (in microliters) and different antigen concentrations is evaluated based on hemagglutination-inhibition (HI) antibody levels and seroconversion in serum of post-hatch chickens at 3 weeks and 4 weeks of age. HI antibody levels were determined as described in Example 4 above. An HI titer of at least 1:40 is considered to be protective. The results are shown in FIGS. 5 and 6.

For A/turkey/Wisconsin/68 (H5N2) influenza monovalent oil emulsion vaccine, group seroconversion was 85–100% for nonconcentrated antigen, 92–100% for 5× concentrated antigen and 91% for 10× concentrated antigen. Mean hemagglutination-inhibition titers ranged from 1:113 to 1:730 for nonconcentrated antigen, from 1:390 to 1:1194 for 5× concentrated antigen and 1:686 to 1:788 for the 10× concentrated antigen.

For Ulster Newcastle Disease virus monovalent emulsion vaccine, group seroconversion was 86 to 100% for nonconcentrated antigen. Seroconversion was 71% to 100% in the multivalent vaccines when adjusted to antigen levels of a nonconcentrated monovalent vaccine.

EXAMPLE 13

Groups of embryonating white leghorn (WL) and white rock (WR) chicken eggs were vaccinated in groups of about 100 as described in Example 5, above, with about 200 to about 600 microliters of a WOW emulsion vaccine containing the Ulster strain of Newcastle disease virus as aqueous antigen in pooled allantoic fluids which was stored at −70° C. until used in the vaccines. Both the metabolizable water-in-oil component and mineral oil water-in-oil component are dispersed in PBS with or without the addition of a 0.5% Tween 80. Approximately 1 part of the water-in-oil component is dispersed in approximately 1 part PBS by syringe and needle. Control groups receive no vaccine. A 23 gauge needle was used to administer the vaccine and the injection depth was approximately 1.5 inches. All vaccinated and control chickens were bled for hemagglutination-inhibition (HI) tests at about 3,4 and 5 weeks posthatch. Eight hemagglutination units were used for the HI tests. Hatchability percent was determined and 10 to 20 vaccinates were selected for HI titers and percent seroconversion response from bleedings at about 3,4 and 5 weeks posthatch. Initially dose volume tolerance was determined in groups given about 200,400 and 600 microliters. Two hundred microliter doses were used as the standard dose, first without antigen concentration and then at about 5 times antigen concentration.

Table 11, a summary of several experiments, below, shows hatchability of white rock chickens, using different formulas of vaccines, as it is affected by dose volume increase using the following described metabolizable oil and mineral oil WOW vaccines containing different surfactant mixtures. Vaccine 1 has a composition of 1 part oil phase emulsified with two parts antigen to form the WO component of the WOW vaccince. The oil phase contains Miglyol 840 (propylene glycol dicaprylate/dicaprate) with 20% surfactant mixture. The surfactant mixture is Marlowet LVS, Imwitor 408 and Imwitor 780K (HULS America) 1:1:1, volume:volume:volume. 1 part of this oil phase is added to 2 parts PBS containing no water soluble surfactant to form the WOW emulsion vaccine. When 200 microliters of vaccine 1 is administered to 100 viable eggs, 96 hatch, giving a hatch rate of 96%. Administering 400 microliters of vaccine 1 to 60 eggs, 58 hatch, giving a hatch rate of 96.66%. Out of 100 control eggs receiving no injection, 97 hatch, giving a hatch rate of 97%.

Vaccine 2 has a composition of 1 part oil phase emulsified with 1 part antigen to form the WO component of the vaccine. The oil phase contains Miglyol 840 with 20% surfactant mixture. The surfactant mixture is Lv4 (Beakin Lv4 which is a complexed lecithin from ADM Co.), Arlacel 80 (Sorbitan monooleate form ICI Co.) And Acconon ca-15 (Ethoxylated caster oil from ABITEC Co.). These are in a 2:2:2 ratio, volume:volume:volume. The HLB of Lv4 =2.0, A80=4.3 and ca-15=16. The HLB of the mixture is 8.66. To form the WO component, 1 part oil phase is emulsified with 1 part antigen. 1 part of the WO component is dispersed in 1 part PBS with 0.5% ca-15 water soluble surfactant. Administering a dose of 200 microliters of vaccine 2 to 102 eggs, 95 hatch, giving a hatch rate of 93%. Administering 400 microliters to 102 eggs, 97 eggs hatch, giving a hatch rate of 95%. When 600 microliters are injected into 60 eggs, 58 hatch, giving a hatch rate of 97%. Of 102 control eggs receiving no injection, 99 hatch, giving a hatch rate of 97%.

Vaccine 3 is the same as vaccine 2 except there is no water soluble surfactant in the PBS phase in which the WOW component is dispersed to form the WOW vaccine. When 200 microliters of vaccine 3 is administered to 100 eggs, 99 hatch, giving a hatch rate of 99%. Administering 400 microliters to 100 eggs, 97 hatch, giving a hatch rate of 97%. Administering 600 microliters to 100 eggs, 93 hatch, giving a hatch rate of 93%. 105 control eggs receiving no injection, 103 hatch, giving a hatch rate of 98%. The results of the three metabolizable vaccines are combined and summarized in Table 11.

Three different mineral oil vaccines were used for the summary of results shown in Table 11 below. Mineral oil vaccine 1 has a composition of 1 part oil phase emulsified with 1 part antigen to form the WO component of the WOW vaccine. The oil phase contains Drakeol 6VR light mineral oil containing 20% of a surfactant mixture. The surfactant mixture is 3 parts Arlacel 80 and 1 part Tween 80. To form the WOW vaccine, 1 part of the WO component is dispersed in 1 part PBS containing 0.5% Tween 80. The WOW vaccine has an HLB=7.0. When 200 microliters of mineral oil vaccine 1 is injected in 100 eggs, 96 hatch, giving a hatch rate of 96%. Administering 400 microliters to 100 eggs, 94 hatch, giving a hatch rate of 94%. Of 100 control eggs receiving no injection, 93 hatch, giving a hatch rate of 93%.

Mineral oil vaccine 2 has a composition of 1 part WO component dispersed in 1 part PBS with no water soluble surfactant. The WO component is made up of 1 part oil phase emulsified with 1 part antigen. The oil phase is Drakeol 6VR light mineral oil with 20% surfactant mixture. The surfactant mixture is 1.3 parts Arlacel 80 and 1 part Tween 80. The HLB of the vaccine is 9.0. When 102 eggs were administered 200 microliters of the vaccine 2, 100 hatched, giving a hatch rate of 98.03%. Administering 400 microliters to 102 eggs, 95 hatch, giving a hatch rate of 93.14%. When 600 microliters are administered to 70 eggs, 64 hatch, giving a hatch rate of 91.43%. 100 eggs hatch out of 102 control eggs receiving no injection giving a hatch rate of 98.03%. Mineral oil vaccine 2 was repeated. Of 100 eggs injected with 200 microliters, 96 hatch, giving a hatch rate of 96%. Of 100 eggs injected with 400 microliters, 94 hatch, giving a hatch rate of 94%. Of 100 egss injected with 600 microliters, 97 hatch, giving a hatch rate of 97%. Of 105 control eggs receiving no injection, 103 hatch, giving a hatch rate of 98.09%. The results of the three mineral oil WOW vaccine experiments are summarized below in Table 11.

Table 11 shows that doses of 200, 400 or 600 microliters in the metabolizable groups only lowered hatchability slightly (approximately 1.4%) in the 200 and 400 microliter groups from the control group. Among groups given mineral oil, vaccine hatchability is lowered approximately 2% by the 400 microliter dose and about 4% by the 600 microliter dose.

Table 12 is a summary of a number of hatches where each hatch receives a different vaccine. 18 day-old white rock chicken embryos were injected with the following metabolizable and mineral oil WOW vaccines. Metabolizable oil vaccine 1 is the same as metabolizable vaccine 1 used to obtain the results above in Table 11.

Vaccine 2 has a WO component that is 1 part oil phase and 1 part aqueous antigen. The oil phase is Miglyol 840 (propylene glycol dicaprylate/dicaprate) with 20% of a surfactant mixture which is Marlowet LVS, Imwitor 408 and Imwitor 780K (HULS America) in a 1:1:1 ratio, volume:volume:volume. 1 part of the WO component is dispersed with 1 part aqueous antigen with 0.5% Acconon ca-15 (ABITEC Co.) water soluble surfactant and 2% performic E (ADM CO.) water soluble lecithin used as a dispersant in instant drinks.

Vaccine 3 uses the same oil phase as metabolizable vaccine 1 used to obtain the results above in Table 11. The WO component is 30% oil phase emulsified in 70% aqueous antigen. 1 part of the WO component is dispersed in 1 part aqueous antigen with no surfactant.

Vaccine 4 is the same as vaccine 2 described immediately above except that the WO component is dispersed in PBS with no surfactant.

Vaccine 5 is the same as metabolizable vaccine 2 used to obtain the results above in Table 11. This vaccine has an HLB of 8.66.

Vaccine 6 is the same as vaccine metabolizable vaccine 1 used to obtain the results above in Table 11 except no surfactant is in the PBS which is used to disperse the WO component to make the WOW vaccine.

Table 12a below presents the results of the six vaccines which are summarized together in Table 12 below.

White leghorn embryos were vaccinated with vaccines 1,2 and 3 as described immediately above. Vaccine 3, for this group of eggs have 1% Tween 80 in the PBS or 1% ca-15 in aqueous antigen into which the WO component is dispersed. These results are presented in Table 12b below and are summarized in Table 12.

For the mineral oil vaccines, vaccine 1 has a WO component that is 50% Drakeol 6VR light mineral oil emulsified in 50% aqueous antigen. 1 part of the WO is dispersed in 1 part PBS with 0.5% Tween 80 to make the WOW mineral oil vaccine. The HLB of the WO component is 7.0.

Vaccine 2 has a WO component of 1 part antigen emulsified in 2 parts Drakeol 6VR light mineral oil with 1 parts Arlacel 80 and 3 parts Tween 80. 1 part of the WO component is dispersed in 1 part PBS with 0.5% Tween 80 and 0.5% PE lecithin. The HLB of the WO component is 7.0.

Vaccine 3 is the same as mineral oil vaccine 1, described immediately above, except the HLB of the WO component is 8.0 by adding a surfactant of 1.9 parts Arlacel 80 and 1 parts Tween 80 to the WO component.

Vaccine 4 is the same as mineral oil vaccine 1, described immediately above, except the HLB of the WO component is 8.0 and the WO component is dispersed in aqueous antigen with 0.5% Tween 80 instead of PBS with 0.5% Tween 80.

Vaccine 5 is the same as vaccine 1, described immediately above, except the HLB of the WO component is 9.0 and the Tween 80 is not added to the PBS that the WO component is dispersed in.

Vaccine 6 is the same as vaccine 1, described immediately above, except the HLB of the WO component is 9.0.

The results of these vaccinations are presented in Table 12c and 12d below for White rock and White leghorn embryos, respectively. Both results are summarized in Table 12 below. Table 12 shows, below, that hatchability varies less than about 1% either higher or lower from control embryos among metabolizable oil-containing vaccine groups and less than about 4% lower among WL vaccinates than the control group among mineral oil vaccinate. Each group received a 200 microliter dose. The metabolizabe oil WOW vaccines contained either of the two surfactant compositions. Percent serconversion (Table 12 below) was about 79% and about 63% for embryos given unconcentrated metabolizable vaccine in WR and WL groups respectively. Percent seroconversion was about 67% and about 82% for WR and WL groups given mineral oil vaccine respectively.

The hatchability and HI response of White rock and White leghorn embryos given mineral oil vaccines with concentrated antigen was determined using five different WOW vaccines.

Mineral oil vaccine 1 has a WO component of 50% Drakeol 6VR light mineral oil emulsified with 50% aqueous antigen concentrated 5 times. The oil phase has 20% surfactants at HLB=8.0. The surfactants are 3 parts Arlacel 80 plus 1 part Tween 80. 1 part WO component is dispersed with 1 part PBS with no water soluble surfactant.

Vaccine 2 is the same as vaccine 1, described immediately above, except that the WO component is dispersed in PBS with 0.5% Tween 80.

Vaccine 3 is the same as vaccine 1, described immediately above, except that the WO component is dispersed in aqueous antigen with no surfactant.

Vaccine 4 is the same as vaccine 1, described immediately above, except that the WO component is at an HLB=9.0.

Vaccine 5 is the same as vaccine 2, described immediately above, except that the WO component is at an HLB=9.0.

The results for White rock and White leghorn embryos are shown below in Tables 13a and 13b, respectively, and are summarized in Table 13. In Table 13, below, hatchability percent varied less than about 2.5% between controls and vaccinates, and percent seroconversion for WR and WL groups given mineral oil emulsion vaccine with concentrated antigen was about 97% and about 82% respectively. The continuous phase is either PBS or aqueous antigen with or without Tween 80 (0.5%). The HLB varied from approximately 8 to approximately 9. Mean titers in Table 13 ranged from about 6.6 to about 7.0.

The result show that large volumes (up to about 600 microliters) of WOW emulsion vaccines can be tolerated by embryos. This allows for enough volume to include many antigen species both in the WO component and in the outer phase of the WOW vaccine.

Seroconversion rates and titers increase with increase of antigen mass as seen by comparing titers in Table XII and XIII below. Increased HLB also increases titers of the vaccine groups probably because the dispersion of the vaccine is increased in the embryo and is more readily processed. TWEEN 80 added to the PBS phase appears to enhance vaccine efficacy because it aids dispersion.

TABLE 11

Effect of wow dose volume on hatchability percent of WR 18-day-old chick embryos

| Vaccine Group | Breed | Number of Hatches | Dose/ul | Total chick Embryo | Number Hatched | Percent Hatched |
|---|---|---|---|---|---|---|
| Metabolizable | WR | 3 | 200 | 302 | 290 | 96.0 |
| | WR | 3 | 400 | 262 | 252 | 96.2 |
| | WR | 2 | 600 | 160 | 151 | 94.4 |
| Control | WR | 3 | 0 | 307 | 300 | 97.7 |
| Mineral Oil | WR | 3 | 200 | 302 | 292 | 96.7 |
| | WR | 3 | 400 | 302 | 283 | 93.7 |
| | WR | 2 | 600 | 170 | 161 | 94.7 |
| Control | WR | 3 | 0 | 307 | 300 | 97.7 |

TABLE 12

Evaluation of wow vaccine in WR and WL 18-day-old chick embryos. Non-concentrated antigen

| VACCINE GROUP | BREED | # OF HATHCES | TOTAL CHICK EMBRYO | NUMBER HATCHED | PERCENT HATCHED | # BLED | % SERO CONVERTERS | MEAN TITER OF SERO CONV. |
|---|---|---|---|---|---|---|---|---|
| Metabolizable | WR | 6 | 970 | 907 | 93.505 | 133 | 76.7 | 4.4 |
| None | WR | 6 | 732 | 691 | 94.399 | 30 | 0 | <1 |
| Metabolizable | WL | 4 | 630 | 597 | 94.762 | 38 | 63 | 3.6 |
| None | WL | 4 | 443 | 422 | 95.260 | 0 | 0 | <1 |
| Mineral Oil | WR | 7 | 1064 | 1030 | 96.805 | 148 | 80.5 | 5.7 |
| None | WR | 7 | 822 | 794 | 96.594 | 47 | 0 | <1 |
| Mineral Oil | WL | 3 | 347 | 328 | 94.524 | 48 | 85.4 | 5.7 |
| None | WL | 3 | 249 | 243 | 97.590 | 10 | 0 | <1 |

TABLE 12A

METABOLIZABLE VACCINE IN WR

| METABOLIZABLE | | HATCHABILITY | | HI | RESPONSE | GROUPS | *SC |
|---|---|---|---|---|---|---|---|
| WR Vaccine | No. Eggs | No. Hat. | % Hat | No./ group | No. SC | % SC | mean HI |
| #1 | 100 | 96 | 96 | 19 | 15 | 79 | 3.7 |
| None | 100 | 97 | 97 | — | — | — | — |
| #2 | 198 | 189 | 95 | 18 | 16 | 89 | 4.4 |
| None | 190 | 177 | 93 | 20 | 0 | 0 | 0.0 |
| #3 | 140 | 123 | 88 | 19 | 17 | 89 | 4.9 |
| #4 | 140 | 126 | 90 | 20 | 17 | 85 | 4.2 |
| None | 140 | 124 | 89 | — | — | — | — |
| #3,1% T80 In PBS disp. | 95 | 90 | 95 | 18 | 12 | 67 | 3.3 |
| #3,1% ca-15 In aaf disp. | 95 | 89 | 94 | 20 | 13 | 65 | 4.7 |

TABLE 12A-continued

METABOLIZABLE VACCINE IN WR

| WR Vaccine | METABOLIZABLE No. Eggs | HATCHABILITY No. Hat. | % Hat | HI RESPONSE No./group | No. SC | GROUPS % SC | *SC mean HI |
|---|---|---|---|---|---|---|---|
| None | 95 | 91 | 96 | — | — | — | — |
| #5 | 102 | 95 | 93 | 10 | 7 | 70 | 4.6 |
| None | 102 | 99 | 98 | 10 | 0 | 0 | 0.0 |
| #6 with *aaf disp. | 100 | 99 | 99 | 9 | 8 | 89 | 5.4 |
| None | No. Surf. 105 | 103 | 98 | — | — | — | — |
| Total vacc | 970 | 907 | 93.5 | 133 | 105 | 76.7 | 4.4 |
| Total none | 732 | 691 | 94.4 | 30 | 0 | 0.0 | 0.0 |

*SC = Seroconversion

TABLE 12B

METABOLIZABLE

Metabolizable vaccine in WL

| WL Vaccine | no. Eggs | no. Hat. | % Hat. | HI No./Group | Response No. SC* | Groups % SC | SC Mean HI |
|---|---|---|---|---|---|---|---|
| #1 | 100 | 96 | 96 | — | — | — | — |
| none | 100 | 98 | 98 | — | — | — | — |
| #2 | 150 | 144 | 96 | 19 | 16 | 84.2 | 4.0 |
| None | 152 | 144 | 94.7 | 20 | 0 | 0.0 | 0.0 |
| #3, 1% T80 in PBS | 90 | 87 | 96.7 | 19 | 8 | 42 | 3.2 |
| #3,1% ca-15 inaaf | 90 | 83 | 92 | 0 | 0 | 0 | 0 |
| none | 90 | 84 | 93 | — | — | — | — |
| #1 with wow (1:1):1 PBS no surf. | 200 | 187 | 93.5 | — | — | — | — |
| none | 101 | 96 | 95 | — | — | — | — |
| Total vac. | 630 | 597 | 94.8 | 38 | 24 | 63 | 3.6 |
| Total none | 443 | 422 | 95.3 | 20 | — | — | — |

*SC = Seroconversion

TABLE 12C

WR mineral oil vaccines. Nonconcentrated antigen.

| GROUPS WR Vaccine no. | HATCHABILITY no. eggs | no. hat. | % hat. | no./ group | HI RESPONSE no. SC | % SC | SC Mean titer |
|---|---|---|---|---|---|---|---|
| #1 | 100 | 96 | 96 | 20 | 12 | 60 | 2.9 |
| None | 100 | 93 | 93 | — | — | — | — |
| #1 | 139 | 133 | 95.7 | 30 | 20 | 67 | 5.5 |
| None | 139 | 134 | 96.4 | 20 | 0 | 0 | 0.0 |
| #2 | 140 | 139 | 99.3 | 20 | 16 | 80 | 5.6 |
| None | 140 | 136 | 97.1 | — | — | — | — |
| #3 | 123 | 118 | 95.9 | 20 | 19 | 95 | 6.6 |
| #4 | 150 | 142 | 94.7 | 20 | 18 | 90 | 5.3 |
| None | 136 | 132 | 97 | — | — | — | — |
| #5 | 105 | 101 | 96.2 | 9 | 8 | 89 | 5.6 |
| #6 | 105 | 101 | 96.2 | 10 | 10 | 100 | 5.5 |
| None | 105 | 101 | 96.2 | 7 | 0 | 0 | 0.0 |
| #6 | 102 | 100 | 98 | 9 | 4 | 44 | 6.2 |
| None | 102 | 99 | 97 | 10 | 0 | 0 | 0.0 |
| #5 | 100 | 100 | 100 | 10 | 10 | 100 | 8.0 |
| None | 100 | 96 | 96 | 10 | 0 | 0 | 0.0 |

TABLE 12C-continued

WR mineral oil vaccines. Nonconcentrated antigen.

| GROUPS WR Vaccine no. | HATCHABILITY no. eggs | no. hat. | % hat. | no./ group | HI RESPONSE no. SC | % SC | SC Mean titer |
|---|---|---|---|---|---|---|---|
| Total vac. | 1064 | 1030 | 96.8 | 148 | 117 | 80.5 | 5.7 |
| Total none | 822 | 794 | 96.6 | 47 | 0 | 0.0 | 0.0 |

TABLE 12D

WL Mineral Oil Vaccines. Nonconcentrated antigen.
Vaccine no.

| Groups WR Vaccine No. | No. eggs | No. hat. | % hat. | no./ group | No. SC* | % SC* | SC* Mean Titer |
|---|---|---|---|---|---|---|---|
| #1 | 75 | 71 | 94.7 | 28 | 25 | 89.2 | 5.7 |
| none | 75 | 74 | 98.7 | 10 | 0 | 0 | 0.0 |

TABLE 12D-continued

WL Mineral Oil Vaccines. Nonconcentrated antigen. Vaccine no.

| Groups WR Vaccine No. | No. eggs | No. hat. | % hat. | no./ group | No. SC* | % SC* | SC* Mean Titer |
|---|---|---|---|---|---|---|---|
| #2 | 80 | 73 | 91.3 | 20 | 16 | 80 | 5.7 |
| none | 77 | 74 | 96.1 | — | — | — | — |
| #3 | 96 | 92 | 95.8 | — | — | — | — |
| #4 | 96 | 92 | 95.8 | — | — | — | — |
| none | 97 | 95 | 97.9 | — | — | — | — |
| Total vac. | 347 | 328 | 94.5 | 48 | 41 | 85.4 | 5.7 |
| Total none | 249 | 243 | 97.6 | 10 | 0 | 0.0 | 0.0 |

*SC = Seroconversion

TABLE 13B-continued

Mineral Oil Vaccine with concentrated Antigen - White Leghorn

| WL Vaccine WR | no. eggs | no. hat. | % hat. | no./ group | no. SC | % SC | SC mean Vacci HI |
|---|---|---|---|---|---|---|---|
| Total vac. | 367 | 355 | 96.7 | 53 | 45 | 86 | 6.7 |
| Total none | 268 | 259 | 96.6 | — | — | — | — |

EXAMPLE 14

Groups of White Rock (WR) chicken eggs were vaccinated in groups of about 100–170 (see Table 14 below) as described in Example 5, above, with about 200 microliters of a WOW emulsion vaccine containing low amounts of aqueous antigen phase, about 20% or less, and high amounts of oil phase, about 80% or more, in the W-O component. The oil phase is increased to compensate for less antigen. The vaccine depth was approximately 1.5 inches. The antigen is the Ulster strain of Newcastle disease virus pooled in allantoic fluids which was stored at −70° C. until used in the vaccines. Both the metabolizable oil water-in-oil component and the mineral oil water-in-oil component are dispersed in PBS without a water soluble surfactant. The mineral oil vaccines were made by emulsifying the antigen in an oil phase containing Drakeol 6vr light mineral oil (Penreco Co., Butler, Pa.) with 10% surfactant which is approximately 3 parts Arlacel 80 and approximately 1 part Tween 80 (ICI Co.). The metabolizable emulsion vaccines are made from Miglyol 810 (a triglyceride oil, Huls America Co.) to which was added 10% surfactant. The surfactant is a mixture of Marlowet LVS (PEG-18 castor oil dioleate), Imwitor 408 (propylene glycol caprylate) and Imwitor 780K (isoteryl diglyceryl succinate) in about a 1:1:1 ratio, volume: volume:volume. The W-O component is dispersed in about an equal volume of PBS with a Waring Blender to formulate a WOW emulsion vaccine. All the vaccines are adjusted to approximately equal antigen mass. To obtain an approximately 1% antigen concentration, about a 20% antigen containing water-in-oil component is mixed with glycerin to remove the water. Glycerin is heavy and easily centrifuged out of the glycerin-W-O mixture. This treatment produces a clear emulsion with a blue haze indicating the presence of small suspended particles (Tyndall effect). This particular emulsion may be considered a microemulsion because of the small particle size.

The results are shown below in Table 14. The data shows that high oil phase—low antigen phase components in the W-O-W portion of the WOW vaccine induce high seroconversion rates in both the oil metabolizable and mineral oil

TABLE 13

Evaluation of wow vaccine in WR and WL 18-day-old chick embryos. Concentrated antigen and surfactant contents at HLB9.

| VACCINE GROUP | BREED | NO. OF HATCHES | TOTAL CHICK EMBRYOS | NUMBER HATCHED | PERCENT HATCHED | NUMBER BLED | % SERO CONVERTERS | MEAN TITER OF SERO CON. |
|---|---|---|---|---|---|---|---|---|
| Mineral Oil | WR | 3 | 605 | 575 | 95.0 | 83 | 96 | 7.0 |
| Non | WR | 3 | 299 | 291 | 97.3 | 7 | 0 | <1 |
| Mineral Oil | WL | 3 | 367 | 355 | 96.7 | 53 | 86 | 6.7 |
| None | WL | 3 | 268 | 259 | 96.6 | 0 | 0 | <1 |

TABLE 13A

Mineral Oil Vaccines with concentrated Antigens - White Rock

| | HATCHABILITY | | | HI RESPONSE GROUPS | | | SC |
|---|---|---|---|---|---|---|---|
| WR | no. eggs | no. hat. | % hat. | no./ group | no. SC | % SC | meanVaccine HI |
| #1 | 100 | 99 | 99 | 14 | 12 | 86 | 7.8 |
| #2 | 100 | 95 | 95 | 15 | 15 | 100 | 6.7 |
| #3 | 100 | 91 | 91 | 14 | 14 | 100 | 6.9 |
| None | 100 | 99 | 99 | — | — | — | — |
| #4 | 100 | 92 | 92 | 15 | 15 | 100 | 7.0 |
| #5 | 100 | 95 | 95 | 15 | 15 | 100 | 6.6 |
| None | 94 | 91 | 96.8 | — | — | — | — |
| #4 | 105 | 103 | 98.1 | 10 | 9 | 90 | 7.0 |
| None | 105 | 101 | 96.2 | 7 | 0 | 0 | 0.0 |
| Total vac. | 605 | 575 | 95 | 83 | 80 | 96 | 7.0 |
| Ttal none | 299 | 291 | 97 | 7 | 0 | 0 | 0.0 |

TABLE 13B

Mineral Oil Vaccine with concentrated Antigen - White Leghorn

| WL Vaccine WR | no. eggs | no. hat. | % hat. | no./ group | no. SC | % SC | SC mean Vacci HI |
|---|---|---|---|---|---|---|---|
| #1 | 100 | 98 | 98 | 14 | 10 | 71 | 7.3 |
| #2 | 100 | 100 | 100 | 15 | 13 | 87 | 6.3 |
| None | 100 | 95 | 95 | — | — | — | — |
| #4 | 75 | 71 | 94.7 | 15 | 13 | 87 | 6.3 |
| None | 75 | 73 | 97.3 | — | — | — | — |
| #4 | 92 | 86 | 93.5 | 9 | 9 | 100 | 6.7 |
| None | 93 | 91 | 97.8 | — | — | — | — | containing WOW vaccines and high titers especially when the antigen mass is increased to 5× concentration. Mineral oil containing W-O-W vaccines with 1% antigen volume in the WO component are effective and high seroconversion rates are obtained in these vaccines with low antigen volume but with equal antigen mass. Furthermore, metabolizable oil containing W-O-W vaccines are comparable in performance to mineral oil containing W-O-W vaccines.

TABLE 14

Hatchability, seroconverstion and HI titer of WR chicken vaccinated as 18-day-old embryos with w-o-w ND emulsion vaccine made from dispersed water-in-oil (W-o) emulsion vaccines containing high oil phase content.
Mineral oil vaccines unconcentrated content.

| Vaccine no. | % oil phase in WO | % ag | no. vacc. | no. hat. | % hat. | no. bled | no. SC | HI GMT weeks postvaccination | | |
|---|---|---|---|---|---|---|---|---|---|---|
| | | | | | | | | 2 | 3 | 4 |
| 1. Drakeol 6vr | 80 | 20 | 132 | 122 | 92 | 15 | 12 | — | 4.8 | 5.2 |
| 2. Drakeol 6vr | 90 | 10 | 132 | 120 | 91 | 15 | 14 | — | 4.6 | 5.3 |
| 3. Drakeol 6vr | 99 | 1 | 132 | 121 | 92 | 15 | 9 | — | 3.7 | 4.8 |
| 4. Control | — | | 132 | 126 | 96 | 13 | 0 | — | <1 | <1 |
| metabolizable vaccine unconcentrated antigen. | | | | | | | | | | |
| 1. Miglyol 810 | 80 | 20 | 100 | 98 | 98 | 15 | 10 | — | 4.5 | 3.8 |
| 2. Miglyol 810 | 90 | 10 | 100 | 95 | 95 | 14 | 13 | — | 4.1 | 3.5 |
| 3. Miglyol 810 | 99 | 1 | 100 | 97 | 97 | 15 | 9 | — | 4.8 | 3.9 |
| 4. Control | — | | 138 | 134 | 97 | 10 | 0 | — | <1 | <1 |
| mineral oil vaccines 5x antigen concentrated. | | | | | | | | | | |
| 1. Drakeol 6vr | 80 | 20 | 118 | 105 | 89 | 15 | 13 | — | 5.5 | 5.9 |
| 2. Drakeol 6vr | 90 | 10 | 118 | 108 | 92 | 15 | 14 | — | 6.0 | 6.5 |
| 3. Drakeol 6vr | 99 | 1 | 118 | 105 | 89 | 15 | 15 | — | 5.9 | 6.5 |
| 4. Control 6vr | — | | 120 | 109 | 91 | 5 | 0 | — | <1 | <1 |
| metabolizable vaccines 5x antigen concentrated. | | | | | | | | | | |
| 1. Miglyol 810 | 80 | 20 | 120 | 103 | 86 | 15 | 12 | — | 5.3 | |
| 2. Miglyol 810 | 90 | 10 | 120 | 109 | 91 | 15 | 11 | — | 5.3 | |
| 3. Miglyol 810 | 99 | 1 | 120 | 105 | 88 | 15 | 11 | — | 4.6 | |
| 4. Control | — | | 170 | 150 | 88 | 5 | 0 | — | <1 | |

EXAMPLE 15

Groups of White Rock (WR) chicken eggs were injected with Ulstee ND aqueous antigen in allantoic amniotic fluid (aaf), phosphate buffered saline (PBS) or water to determine the effects of the various diluents as well as the quantities on hatch rate of chicks. These preparations can be used as the second aqueous phase into which the WO component is mixed to form the W-O-W vaccine. Results are shown in Table 15 below.

Embryos will tolerate much more aaf antigen than is needed in the WOW vaccines. This is expected since aaf is a normal constituent of the embryos. PBS is a common diluent for various antigens and appears to be compatible for embryo injection. Water also appears to be well tolerated by the embryos and possibly could be used to relieve dehydration stress from long shipments or may be the choice of media to disperse water-in-oil emulsion to prepare the W-O-W vaccine.

EXAMPLE 16

Groups of White Rock chicken eggs were injected with chicken antisera (AS), chicken serum gamma globulin (S-GG) or chicken yolk gamma globulin (Y-66) prepared as described in Example 2 above. The results are shown in FIG. 7.

Injecting antiserum or antibody preparations into embryos as shown in FIG. 7 shows that the posthatch chick has protective levels of antibodies at 1-day of age and later and no doubt at hatch time. This is a way of establishing passive immunity at the very earliest with antibody. WO vaccines can be dispersed in aqueous media containing antibodies and such a wow vaccine could thus provide passive immunity for the short term and active immunity for the longer term. Protection could be against several disease entities either in homologous or heterologous combinations with the vaccines since hens can be hyper immunized concomitantly against various avian diseases with combined or multivalent vaccines and their egg yolk antibodies harvested for many immunological applications.

The foregoing detailed description is for the purpose of illustration. Such detail is solely for that purpose and those skilled in the art can make variations therein without departing from the spirit and scope of the invention.

TABLE 15

Effect on hatchability of injecting Ulster ND aqueous antigen in aaf, PBS water into 18-day-old WR embryos.

| media | ul dose | no./ group | no. hat. | % hat. |
|---|---|---|---|---|
| aaf | 200 | 115 | 111 | 97 |
| aaf | 400 | 115 | 108 | 94 |
| aaf | 600 | 115 | 110 | 96 |
| PBS | 600 | 50 | 48 | 96 |
| water | 600 | 46 | 45 | 98 |
| non | 0.0 | 116 | 113 | 97 |

1. Injection depth was 1.5 inches with a 23 gauge needle.

INDEX OF THE ELEMENTS DESIGNATED BY A NUMERAL

1. Air Cell
2. Allantoic Cavity
3. Amniotic Cavity
4. Albumin
5. Yolk Sac
6. Embryo
7. Shell Membrane
8. Needle
9. Syringe
10. Egg

I claim:

1. A method for in ovo immunization of an avian species comprising
   puncturing an egg of said avian species with a puncturing means at the longitudinal midline over said egg's air cell in order to administer a water-in-oil-in-water emulsion vaccine in said egg's albumin end, injecting said water-in-oil-in-water emulsion vaccine into the egg by vertically inserting a needle means through said air cell to the albumin end,
   administering said vaccine into the albumen end of the egg, and
   hatching said egg to obtain an immunized avian species.

2. The method of claim 1 wherein said egg is selected from the group consisting of chicken eggs, turkey eggs, geese eggs, duck eggs, and pheasant eggs.

3. The method of claim 1 wherein said vaccine is selected from the group consisting of monovalent and polyvalent vaccines.

4. The method of claim 1 wherein said vaccine confers immunity against microbial diseases.

5. The method of claim 4 wherein said diseases include Newcastle's disease, avian influenza, avian leukosis, infectious bursal disease, adenovirus disease, reovirus, pox, laryngotracheitis, infectious bronchitis, reticuloendotheliosis, infectious coryza, fowl typhoid, fowl cholera, Salmonella, and Marek's disease.

6. The method of claim 1 wherein the vaccine is administered at a dose of from about 20 microliters to about 600 microliters.

7. The method of claim 1 wherein said vaccine is in a concentration of from about 1× to about 10×.

* * * * *